(12) United States Patent
Torti et al.

(10) Patent No.: US 8,252,772 B2
(45) Date of Patent: Aug. 28, 2012

(54) HYPERTHERMIC TECHNOLOGIES AND THERAPEUTIC USES THEREOF

(75) Inventors: Suzy Torti, Winston-Salem, NC (US); Frank Torti, Winston-Salem, NC (US); David Loren Carroll, Winston-Salem, NC (US); Steven Akman, Greensboro, NC (US); Omkaram Nalamasu, San Jose, CA (US); Pulickel Ajayan, Houston, TX (US)

(73) Assignee: Wake Forest University, Winston Salem, NC (US)

( * ) Notice: Subject to any disclaimer, the term of this patent is extended or adjusted under 35 U.S.C. 154(b) by 483 days.

(21) Appl. No.: 12/302,382

(22) PCT Filed: May 25, 2007

(86) PCT No.: PCT/US2007/012492
§ 371 (c)(1),
(2), (4) Date: Nov. 16, 2009

(87) PCT Pub. No.: WO2007/139936
PCT Pub. Date: Dec. 6, 2007

(65) Prior Publication Data
US 2010/0075925 A1   Mar. 25, 2010

Related U.S. Application Data

(60) Provisional application No. 60/808,399, filed on May 25, 2006, provisional application No. 60/854,500, filed on Oct. 26, 2006.

(51) Int. Cl.
*A61K 31/69* (2006.01)
*A61K 31/13* (2006.01)
(52) U.S. Cl. ........... 514/64; 514/579; 977/742; 977/915
(58) Field of Classification Search .................... 514/64, 514/579; 977/742, 915
See application file for complete search history.

(56) References Cited

U.S. PATENT DOCUMENTS

| | | |
|---|---|---|
| 2003/0180491 A1 | 9/2003 | Hirsch et al. |
| 2005/0152891 A1 | 7/2005 | Toone et al. |
| 2006/0051290 A1 | 3/2006 | Wilson et al. |

FOREIGN PATENT DOCUMENTS

| | | |
|---|---|---|
| JP | 2005075720 A | 3/2005 |
| KR | 2006016601 A | 2/2006 |
| WO | 03084869 A | 10/2003 |
| WO | 2005097672 A | 10/2005 |
| WO | 2006099445 A | 9/2006 |

OTHER PUBLICATIONS

International Search Report mailed on Nov. 15, 2007 in International Application No. PCT/US2007/012492.
Clare Sansom, Nanotechnology used to kill tumour cells, Lancet Oncology, Sep. 2005, p. 641, vol. 6, No. 9, Lancet Publishing Group, London, GB.
Nadine Wong Shi Kam et al, Carbon nanotubes as multifunctional biological transporters and near-infrared agents for selective cancer destruction, Proceedings of the National Academy of Sciences of USA, Aug. 16, 2005, pp. 11600-11605, vol. 102, No. 33, National Academy of Science, Washington, DC.
Zhu Yinghuai et al, Substituted Carborane-Appended Water Soluable Single-Wall Carbon Nanotubes: New Approach to Boron Neutron Capture Therapy Drug Delivery, Journal of the American Chemical Society, Jun. 16, 2005, pp. 9875-9880, vol. 127, American Chemical Society.
International Search Report mailed on Sep. 29, 2008 in International Application No. PCT/US2008/003332.

*Primary Examiner* — Raymond Henly, III
(74) *Attorney, Agent, or Firm* — J. Clinton Wimbish; Smith Moore Leatherwood LLP

(57) ABSTRACT

The present invention provides nanoscale and microscale compositions useful for a variety of purposes, including the diagnosis and treatment of diseases. In one embodiment, the present invention provides a disease treatment system comprising a thermal induction agent and a radiation source, wherein the thermal induction agent comprises at least one carbon nanotube, at least one carbon microtube, or a mixture thereof.

18 Claims, 24 Drawing Sheets

HYPERTHERMIC TECHNOLOGIES AND THERAPEUTIC USES THEREOF

PRIOR RELATED APPLICATIONS

This application hereby claims priority to U.S. Provisional Patent Application Ser. No. 60/808,399, filed May 25, 2006 and U.S. Provisional Patent Application Ser. No. 60/854,500, filed Oct. 26, 2006.

STATEMENT OF GOVERNMENT LICENSE RIGHTS

This invention was made through the support of the Department of Defense—United States Air Force Office of Scientific Research (AFOSR) Grant No. FA9550-04-1-0161. The Federal Government may retain certain license rights in this invention.

FIELD OF THE INVENTION

The present invention relates to embodiments of hyperthermic technologies, including nanostructures and microstructures, and therapeutic uses for the same in medical fields including imaging and treatment of disease.

BACKGROUND OF THE INVENTION

Carbon nanotubes, in general, are cylinders of graphite closed at each end with caps containing six pentagonal rings. Carbon nanotubes can be conceptually illustrated by dividing a fullerene ($C_{60}$) in half and placing a graphene cylinder between the two halves. Dividing the fullerene parallel to one of the three-fold axes results in a zig-zag nanotube construction while dividing the fullerene along one of the five-fold axes produces an armchair nanotube construction. In addition to varying lattice geometries, carbon nanotubes demonstrate different macrostructures expressed as single-walled nanotubes and multi-walled nanotubes.

Since their discovery in 1991, carbon nanotubes have found application in a wide variety of fields due to their distinct and advantageous electronic and mechanical properties. One field in which nanotubes are finding continued applicability is that of biomaterials. Carbon nanotubes have been used for electrochemical detection of biological species, tissue scaffolding, and molecular delivery. Single-walled carbon nanotubes have been shown to shuttle various cargoes across cellular membranes without cytotoxicity thereby providing additional avenues for drug delivery in disease treatment applications.

Many diseases exist which require harsh treatment strategies and procedures. One such disease is cancer. Despite considerable research efforts, cancer remains one of the leading causes of death in the United States. Treatments for cancer are invasive and generally include surgery to remove cancerous tissue followed by radiation and/or chemotherapy. Cancer treatments often produce harmful side effects such as undifferentiated destruction of diseased and healthy cells, fatigue, nausea, and vomiting.

In view of these harmful side effects, it would be desirable to provide alternative, less invasive treatment strategies for cancer and other diseases. It would additionally be desirable to provide carbon nanoparticle compositions operable for use in such strategies.

SUMMARY

The present invention provides new multifunctional nanoscale and microscale compositions. The compositions may, among other uses, be advantageously used to perform one or more of the following functions in a therapeutic method: targeting selected cells, imaging cells, and/or inducing hyperthermia in selected cells.

In one aspect, the present invention provides carbon nanoparticle compositions, including carbon nanotubes, and methods of making the same. The present invention also provides systems and methods incorporating carbon nanoparticle compositions described herein for the treatment of diseases including, but not limited to, cancer.

In one embodiment, a nanoparticle composition comprises a carbon nanotube comprising iron, wherein the nanotube has a diameter ranging from about 5 nm to about 100 nm. In some embodiments, a carbon nanotube comprising iron has a length ranging from about 500 nm to about 1500 nm. A carbon nanotube comprising iron, in some embodiments, is doped with nitrogen and/or boron. Carbon nanotubes can comprise single-walled carbon nanotubes (SWNT), multi-walled carbon nanotubes (MWNT), or mixtures thereof.

In another embodiment, a nanoparticle composition comprises a carbon nanotube comprising iron and at least one positive magnetic resonance (T1) contrast agent. In some embodiments, a positive contrast agent includes chemical species comprising gadolinium, such as gadolinium chloride. In some embodiments, carbon nanotubes comprising iron and a positive contrast agent are doped with nitrogen and/or boron.

In some embodiments, carbon nanotubes provided herein comprise substantially no iron. In one embodiment, for example, a carbon nanotube does not comprise iron and is doped with nitrogen and/or boron.

In another embodiment, a nanoparticle composition comprises carbon nanotubes having branched structures. Branched structures, according to embodiments of the present invention, comprise multiple branches, multiple branches with multiple branches, Y branches, Y branches with multiple branches, and multilevel Y branches. Carbon nanotubes having branched structures, in some embodiments, can comprise at least one metal particle or a plurality of metal particles.

In a further embodiment, a nanoparticle composition comprises a spherical or faceted substrate and a plurality of carbon nanotubes coupled to the substrate. In some embodiments, the substrate can comprise silica, iron, or alloys of metals including iron, nickel, copper, gadolinium, and dysprosium. In some embodiments, the substrate can comprise composites of silica and metals as provided herein. Nanotubes coupled to the spherical or faceted substrate, in some embodiments, comprise iron, other transition metals and alloys thereof.

In another aspect, the present invention provides microparticle compositions. The present invention also provides systems and methods incorporating carbon microparticle compositions described herein for the treatment of diseases including, but not limited to, cancer.

In one embodiment, a microparticle composition comprises one or a plurality of carbon microparticles. Carbon microparticles, according to some embodiments, comprise carbon microtubes. In one embodiment, carbon microtubes comprise iron. In another embodiment, carbon microtubes are doped with nitrogen and/or boron. Carbon microtubes can comprise single-walled carbon microtubes, multi-walled carbon microtubes, or mixtures thereof.

Carbon microtubes, according to some embodiments of the present invention, have lengths greater than 1 µm. In one embodiment, a carbon microtube has a length ranging from 1 µm to about 100 µm, from about 5 µm to about 90 µm, from about 10 µm to about 75 µm, or from about 20 µm to about 60

µm. In another embodiment, a carbon microtube has a length ranging from 1 µm to about 15 µm or from about 5 µm to about 10 µm. In a further embodiment, a carbon microtube has a length greater than about 100 µm. In one embodiment, a carbon microtube has a length ranging from about 50 µm to about 100 µm.

A carbon microtube, in some embodiments, has a diameter ranging from about 5 nm to about 150 nm. In another embodiment, a carbon microtube has a diameter ranging from about 10 nm to about 100 nm, from about 20 nm to about 80 nm, or from about 40 nm to about 70 nm. In a further embodiment, a carbon microtube has a diameter greater than about 150 nm.

A carbon microtube, according to some embodiments of the present invention, is bent, curved, and/or folded. In one embodiment, a bent, curved, and/or folded microtube has a substantially spherical structure or shape.

A bent, curved, and/or folded carbon microtube, in some embodiments, has a radius of gyration ranging from about 1 µm to about 100 µm, from about 5 µm to about 80 µm, from about 10 µm to about 70 µm, from about 20 µm to about 60, or from about 30 µm to about 50 µm. In another embodiment, a bent, curved, and/or folded carbon microtube has a radius of gyration greater than about 100 µm. In some embodiments, a bent, curved, and/or folded microtube has a substantially spherical shape.

A bent, curved, and/or folded carbon microtube, according to some embodiments of the present invention, further comprises a polymeric or surfactant component. The polymeric or surfactant component may assist in maintaining the bent, curved, and/or folded structure of the carbon microtube. In some embodiments, a polymeric component comprises one or a plurality of polymeric materials including, but not limited to, alginate, polymethylmethacrylate, poly(D,L-lactide-co-glycolide) (PLGA), collagen, or combinations thereof. In some embodiments, the polymeric material is cross-linked thereby providing enhanced stability to the bent, curved, and/or folded structure of the carbon microparticle. In other embodiments, a surfactant component comprises one or a plurality of surfactants. Surfactants, according to embodiments of the present invention comprise anionic surfactants, cationic surfactants, nonionic surfactants, or combinations thereof. In some embodiments, lipids and/or other biomolecules may assist in maintaining the bent, curved, and/or folded structure of a carbon microtube.

Bent, curved, and/or folded carbon microtubes, in some embodiments, are produced by ultrasonicating the carbon microtubes in a solution comprising the polymeric or surfactant component.

In another aspect, compositions of the present invention comprise carbon nanoparticles and/or carbon microparticles having at least one surface functionalized with at least one hydrophilic chemical species. In one embodiment, for example, a nanoparticle composition comprises a carbon nanotube having at least one surface functionalized with at least one hydrophilic chemical species. Carbon nanotubes having at least one surface functionalized with at least one hydrophilic chemical species, in some embodiments, can comprise branched and unbranched carbon nanotubes.

In another embodiment, a microparticle composition comprises a carbon microtube having at least one surface functionalized with at least one hydrophilic chemical species. Carbon microtubes having at least one surface functionalized with at least one hydrophilic chemical species, in some embodiments, comprise bent, curved, and/or folded carbon microtubes.

Hydrophilic chemical species suitable for functionalizing at least one surface of a carbon nanotube or microtube, in one embodiment, can comprise species having carboxyl groups (COOH). In other embodiments, suitable hydrophilic chemical species can comprise hydrophilic polymers such as, but not limited to, poly(dimethyldiallylammonium chloride), polyethylene glycol, alkoxylated polyethylene glycol, or polypropylene glycol.

In some embodiments, at least one surface of a carbon nanotube or a carbon microtube is functionalized by covalently linking a hydrophilic chemical species to the surface. In other embodiments, at least one surface of a carbon nanotube or a carbon microtube is functionalized by forming non-covalent intermolecular interactions with a hydrophilic chemical species, including ionic, dipole-dipole, and/or Van der Waals interactions. In a further embodiment, at least one surface of a carbon nanotube or a carbon microtube is functionalized by forming covalent and non-covalent interactions with one or more hydrophilic chemical species. Functionalization of at least one surface of carbon nanotubes or carbon microtubes with hydrophilic chemical species can increase the solubility and dispersion of the nanotubes and microtubes in polar media.

In another aspect, the present invention provides methods of producing carbon nanotubes and carbon microtubes. In one embodiment, a method for producing carbon nanotubes or carbon microtubes comprises providing a solution comprising a carbon source and an iron source, injecting the solution into a preheater, vaporizing the solution, transporting the solution to a furnace in a carrier gas, and pyrolyzing the solution. In some embodiments, a solution comprising a carbon source and an iron source can further comprise a boron and/or nitrogen source.

In another embodiment, a method for producing branched carbon nanotubes comprises providing an anodized template comprising branched pore structures and synthesizing carbon nanotubes within the branched pore structures of the template. In some embodiments, a method for producing branched carbon nanotubes further comprises electrodepositing at least one metal inside the carbon nanotubes. In a further embodiment, a method for producing branched carbon nanotubes further comprises removing the template. Branched carbon nanotubes, according to methods of the present invention, comprise nanotubes having multiple branches, multiple branches with multiple branches, Y branches, Y branches with multiple branches, and multilevel Y branches.

The present invention additionally provides methods of modulating carbon nanotube or carbon microtube properties. In one embodiment, a method comprises modulating carbon nanotube or carbon microtube thermal induction, wherein modulating comprises doping carbon nanotubes or carbon microtubes with nitrogen, boron, or combinations thereof. In another embodiment, a method comprises modulating carbon nanotube or carbon microtube ablation threshold, wherein modulating comprises doping carbon nanotubes or carbon microtubes with nitrogen, boron, or combinations thereof.

In related embodiments, the present invention provides methods for heating and ablating carbon nanotubes or carbon microtubes. In an embodiment, a method for heating and ablating a carbon nanotube or a carbon microtube comprises irradiating the carbon nanotube or the carbon microtube with a radiation source.

In another aspect, the present invention provides systems and methods for the treatment of diseases incorporating carbon nanoparticles and/or carbon microparticles. Carbon nanoparticles, in some embodiments of systems and methods of the present invention, comprise carbon nanotubes. Moreover, carbon microparticles, in some embodiments of systems and methods of the present invention, comprise carbon microtubes. In some embodiments, carbon microtubes demonstrate a bent, curved, and/or folded architecture.

In one embodiment, the present invention comprises a system for the treatment of disease comprising a thermal induction agent and a radiation source, wherein the thermal induction agent comprises at least one carbon nanoparticle and/or carbon microparticle. In such embodiments, the thermal induction agent can be operable to express a giant oscillator strength for enhanced coupling to the radiation field. In some embodiments, the thermal induction agent can be ablated by radiation from the radiation source. For microwave ablation, oscillator strengths can be 0.5 the wavelength of cm or about 0.5 cm. For infrared ablation, oscillator strengths can be as long as 700 nm. In some embodiments, the carbon nanoparticle comprises a carbon nanotube. Additionally, in some embodiments, a carbon microparticle comprises a carbon microtube. In one embodiment, a carbon microtube has a bent, curved, and/or folded structure.

In another embodiment, the present invention provides a disease imaging system comprising a magnetic field source, a radiation source, and a thermally inducting contrast agent, wherein the contrast agent comprises at least one carbon nanoparticle and/or carbon microparticle, wherein the nanoparticle and/or microparticle comprises iron. The carbon nanoparticle, in some embodiments, comprises a carbon nanotube. Moreover, the carbon microtube, in some embodiments, comprises a carbon microtube. In one embodiment, a carbon microtube has a bent, curved, and/or folded structure.

In another aspect, the present invention provides methods of treating disease. In one embodiment, a method of treating disease comprises disposing at least one carbon nanoparticle and/or carbon microparticle in a biological environment and heating the biological environment using the carbon nanoparticle and/or carbon microparticle. The carbon nanoparticle, in some embodiments, comprises a carbon nanotube. Moreover, the carbon microparticle, in some embodiments, comprises a carbon microtube. In one embodiment, a carbon microtube has a bent, curved, and/or folded structure.

In another embodiment, a method for imaging and treating disease comprises disposing at least one carbon nanoparticle and/or carbon microparticle comprising iron in a biological environment, imaging the biological environment using the carbon nanoparticle and/or carbon microparticle, and heating the biological environment using the carbon nanoparticle and/or carbon microparticle. Imaging, in some embodiments, comprises inducing a magnetic field, disposing the biological environment in the induced magnetic field, and irradiating the biological environment with a radio frequency.

In a further aspect, the present invention also provides systems and methods of delivering pharmaceutical compositions to a biological environment. In one embodiment, a system for delivering pharmaceutical compositions comprises a pharmaceutical composition disposed in a casing and a radiation source, wherein the casing comprises a plurality of nanoparticles and/or microparticles dispersed in a matrix comprising poly(diallyldimethylammonium) (PDDA) and/or salt thereof. In another embodiment, a method of delivering a pharmaceutical composition comprises administering a pharmaceutical composition disposed in a casing to an individual and ablating the casing to at least partially release the pharmaceutical composition. Ablating the casing, in some embodiments, comprises irradiating the casing with a radiation source.

These and other embodiments of the present invention are described in greater detail in the detailed description of the invention which follows.

DETAILED DESCRIPTION

Figure 1:
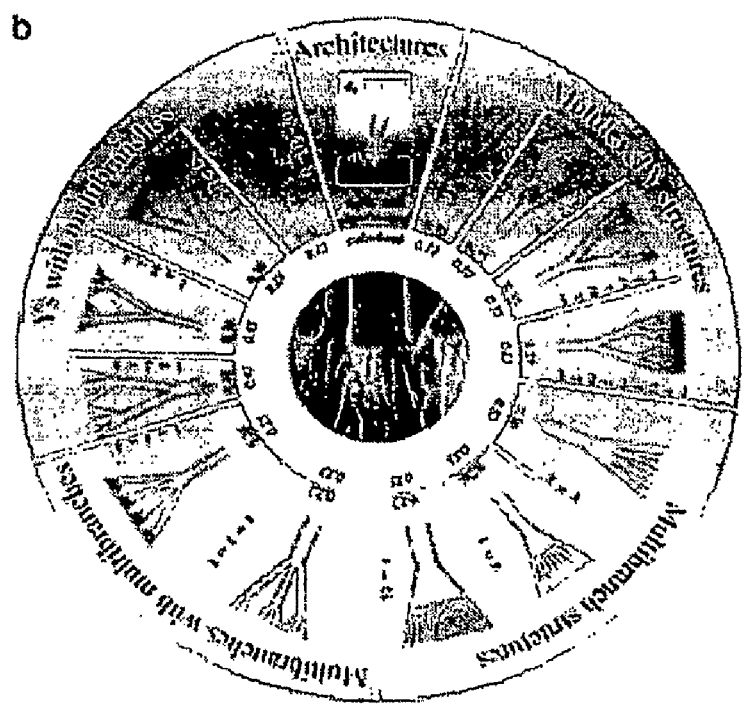
FIG. 1 illustrates carbon nanotube branching according to embodiments of the present invention.

For the purposes of this specification, unless otherwise indicated, all numbers expressing quantities of ingredients, reaction conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to any claims that might be filed in applications claiming priority to this application, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent.

Further, when the phrase "up to" is used in connection with an amount of a component, material, or composition in the claims, it is to be understood that the component, material, or composition is present in at least a detectable amount (e.g., its presence can be determined) and may be present up to and including the specified amount.

The present invention provides nanoscale and microscale compositions useful for a variety of purposes, including the diagnosis and treatment of diseases. In one embodiment, the present invention provides carbon nanoparticle compositions, including carbon nanotubes, as well as methods of making and using the same. In another embodiment, the present invention provides carbon microparticle composition, including carbon microtubes, and methods of making and using the same. The present invention additionally provides systems and methods incorporating carbon nanoparticle and carbon microparticle compositions described herein for the treatment of diseases.

In one aspect, the present invention provides a nanoparticle composition comprising a carbon nanotube comprising iron, wherein the carbon nanotube has a diameter ranging from about 5 nm to about 100 nm. In some embodiments, a carbon nanotube can have a diameter ranging from about 10 nm to about 30 nm. In other embodiments, a carbon nanotube can have a diameter ranging from greater than 50 nm to about 100 nm. In a further embodiment, a carbon nanotube can have a diameter ranging from about 70 nm to about 100 nm.

Carbon nanotubes comprising iron, in some embodiments, can have lengths ranging from about 500 nm to about 1500 nm. In other embodiments, carbon nanotubes comprising iron can have lengths ranging from about 800 nm to about 1200 nm.

Carbon nanotubes comprising iron, according to some embodiments, comprise at least 0.1 percent, by weight iron. In other embodiments, carbon nanotubes comprising iron can comprise greater than about 2 percent, by weight iron. In a further embodiment, a carbon nanotube comprises an iron content ranging from about 0.1 percent, by weight to about 2 percent, by weight.

In some embodiments, carbon nanotubes comprising iron can comprise single-walled nanotubes. In other embodiments, carbon nanotubes comprising iron can comprise multi-walled nanotubes. Carbon nanotubes comprising iron, in a further embodiment, can comprise branched nanotubes. Branched nanotubes, according to embodiments of the present invention, comprise single-walled and multi-walled carbon nanotubes having multiple branches, multiple branches with multiple branches, Y branches, Y branches with multiple branches, and multilevel Y branches. FIG. 1 illustrates carbon nanotube branching architectures according to embodiments of the present invention.

In some embodiments of carbon nanotubes comprising iron, the iron can comprise one or more particles disposed in a cavity formed by the nanotube. In one embodiment, an iron particle can be disposed in the central cavity of a carbon nanotube. A plurality of iron particles, according to some embodiments, can be disposed in the central cavity of a carbon nanotube at regular intervals, such as 100 nm intervals. In other embodiments, iron particles can be disposed between the walls of a multi-walled carbon nanotube or throughout the branches of a branched carbon nanotube.

Alternatively, in another embodiment, an iron particle may be disposed on an outer surface of a carbon nanotube. In a further embodiment, one or more iron particles may be incorporated into the lattice of a carbon nanotube.

Iron particles, according to embodiments of the present invention, can range from a single iron atom to a cluster comprising a plurality of iron atoms. In some embodiments, iron clusters can have diameters ranging from about 2 nm to about 50 nm.

Moreover, in one embodiment, carbon nanotubes having any of the constructions provided herein comprise substantially no iron. In another embodiment, carbon nanotubes do not comprise iron.

In another embodiment, a carbon nanotube can comprise at least one magnetic resonance contrast agent. In some embodiments, the at least one magnetic resonance contrast agent is a positive (T1) contrast agent. A positive contrast agent, in some embodiments, comprises chemical species comprising gadolinium, such as gadolinium chloride ($GdCl_3$). In one embodiment, the at least one magnetic resonance contrast agent is disposed within the nanotube. In another embodiment, the at least one magnetic resonance contrast is disposed on a surface of the carbon nanotube.

Carbon nanotubes, according to some embodiments, can be doped with boron nitrogen, or combinations thereof. In one embodiment, doped carbon nanotubes can comprise boron in amount ranging from about 0.01 percent, by weight to about 10 percent, by weight. In another embodiment, doped carbon nanotubes can comprise about 5 percent, by weight boron. In other embodiments, doped carbon nanotubes can comprise nitrogen in an amount ranging from about 0.01 percent, by weight, to about 30 percent, by weight or from about 5 percent, by weight, to about 25 percent, by weight. In another embodiment, doped carbon nanotubes can comprise nitrogen in an amount greater than about 30 percent, by weight. In another embodiment, doped carbon nanotubes can comprise from about 10 percent, by weight nitrogen to about 20 percent, by weight nitrogen. In a further embodiment, doped carbon nanotubes can comprise less than about 1 percent, by weight nitrogen. In some embodiments, doped carbon nanotubes can comprise between about 5 percent, by weight and about 10 percent by weight boron and/or nitrogen.

In another aspect, the present invention provides microparticle compositions. In one embodiment, a microparticle composition comprises one or a plurality of carbon microparticles. Carbon microparticles, according to some embodiments of the present invention, comprise carbon microtubes. Carbon microtubes, in some embodiments, comprise iron. In some embodiments, carbon microtubes are doped with nitrogen and/or boron. Carbon microtubes can comprise single-walled carbon microtubes, multi-walled carbon microtubes, or mixtures thereof.

Carbon microtubes, according to some embodiments of the present invention, have lengths greater than 1 µm. In one embodiment, a carbon microtube has a length ranging from 1 µm to about 100 µm, from about 5 µm to about 90 µm, from about 10 µm to about 75 µm, or from about 20 µm to about 60 µm. In another embodiment, a carbon microtube has a length ranging from 1 µm to about 15 µm or from about 5 µm to about 10 µm. In a further embodiment, a carbon microtube has a length greater than about 100 µm.

A carbon microtube, in some embodiments, has a diameter ranging from about 5 nm to about 150 nm. In another embodiment, a carbon microtube has a diameter ranging from about 10 nm to about 100 nm, from about 20 nm to about 80 nm, or from about 40 nm to about 70 nm. In a further embodiment, a carbon microtube has a diameter greater than about 150 nm.

A carbon microtube, according to some embodiments, is bent, curved, and/or folded. A bent, curved, and/or folded carbon microtube, in some embodiments, has a radius of gyration ranging from about 1 µm to about 100 µm, from about 5 µm to about 80 µm, from about 10 µm to about 70 µm, from about 20 µm to about 60, or from about 30 µm to about 50 µm. In another embodiment, a bent, curved, and/or folded carbon microtube has a radius of gyration greater than about 10 µm. In some embodiments, a bent, curved, and/or folded microtube has a substantially spherical shape.

A bent, curved, and/or folded carbon microtube, according to some embodiments of the present invention, further comprises a polymeric or surfactant component. The polymeric or surfactant component, in some embodiments, may assist in maintaining the bent, curved, and/or folded structure of the carbon microtube. In some embodiments, a polymeric component comprises one or a plurality of polymeric materials including, but not limited to, alginate, polymethylmethacrylate, poly(D,L-lactide-co-glycolide) (PLGA), collagen, or combinations thereof. In some embodiments, the polymeric material is cross-linked thereby providing enhanced stability to the bent, curved, and/or folded structure of the carbon microparticle. In other embodiments, a surfactant component comprises one or a plurality of surfactants. Surfactants, according to embodiments of the present invention comprise anionic surfactants, cationic surfactants, nonionic surfactants, or combinations thereof. In some embodiments, lipids and/or other biomolecules may assist in maintaining the bent, curved, and/or folded structure of the carbon microtube.

Bent, curved, and/or folded carbon microtubes, in some embodiments, are produced by ultrasonicating the carbon microtubes in a solution comprising the polymeric or surfactant component. Depending on the degree of bending, curving, and/or folding desired, carbon microtubes, in some embodiments, are ultrasonicated in a solution comprising the polymeric or surfactant component from about 1 minute to about 72 hours. In one embodiment, carbon microtubes are ultrasonicated in a solution comprising the polymeric or surfactant component for about 24 hours.

Figure 2:
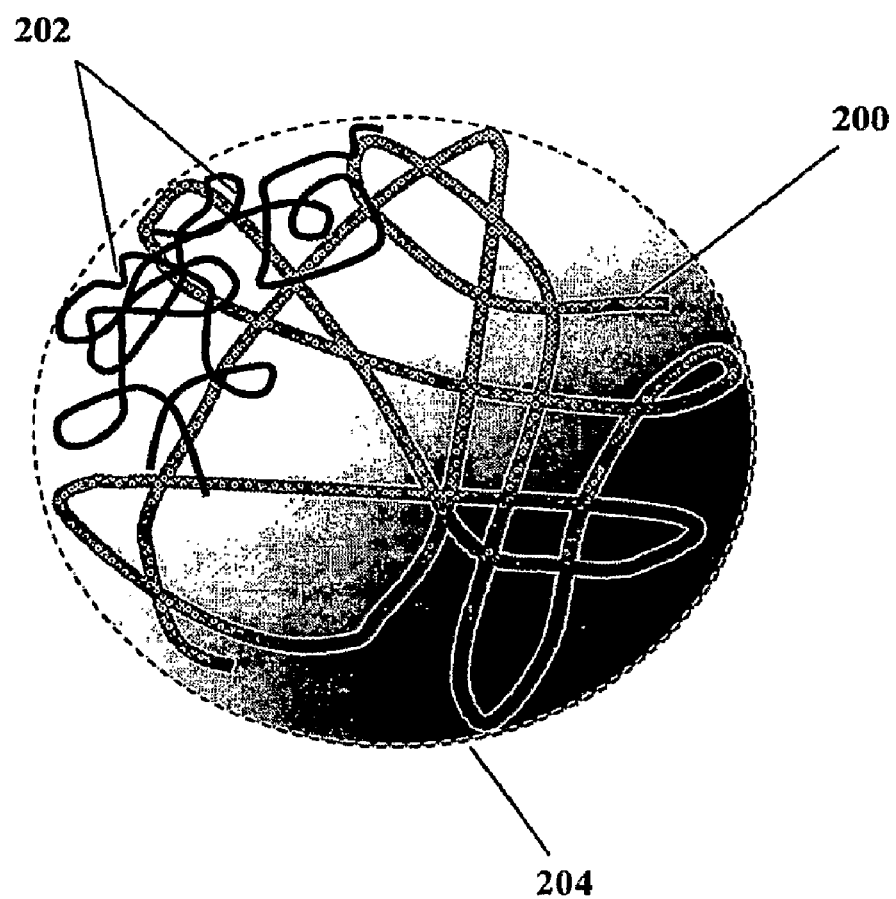
FIG. 2 illustrates a carbon microtube according to one embodiment of the present invention.

FIG. 2 is a schematic of a bent, curved, and/or folded carbon microtube according to one embodiment of the present invention. The bent, curved, and/or folded carbon microtube (200) is entangled with a polymeric or surfactant component (202). The polymeric or surfactant component (202) may assist in maintaining the bent, curved, and/or folded architecture of the microtube (200). The microtube (200) can additionally demonstrate a radius of gyration (204) ranging from about 1 µm to about 100 µm.

Figure 3:
FIG. 3 illustrates a carbon microtube according to one embodiment of the present invention.

FIG. 3 is a TEM image of curved microtubes according to one embodiment of the present invention. The microtubes of FIG. 3 were produced by chemical vapor deposition (CVD), as provided herein, disposed in a chloroform solvent, and ultrasonicated for about 20 minutes with a horn sonicator at high power in the presence of surfactants or polymers.

In some embodiments, carbon microtubes comprise iron. In one embodiment, a carbon microtube comprises at least 0.1 percent, by weight iron. In another embodiment, a carbon microtube comprises greater than about 2 percent by weight iron. In a further embodiment, a carbon microtube comprises an iron content ranging from about 0.1 percent, by weight to about 2 percent, by weight.

In some embodiments of carbon microtubes comprising iron, the iron can comprise one or more particles disposed in a cavity formed by the microtube. In one embodiment, an iron particle can be disposed in the central cavity of a carbon microtube. A plurality of iron particles, according to some embodiments, can be disposed in the central cavity of a carbon microtube at regular intervals, such as 100 nm intervals. In other embodiments, iron particles can be disposed in the walls of a carbon microtube.

Alternatively, in another embodiment, an iron particle may be disposed on an outer surface of a carbon microtube. In a further embodiment, one or more iron particles may be incorporated into the lattice of a carbon microtube.

Iron particles, according to embodiments of the present invention, can range from a single iron atom to a cluster comprising a plurality of iron atoms. In some embodiments, iron clusters can have diameters ranging from about 2 nm to about 50 nm.

In another embodiment, a carbon microtube can comprise at least one magnetic resonance contrast agent. In some embodiments, the at least one magnetic resonance contrast agent is a positive (T1) contrast agent. A positive contrast agent, in some embodiments, comprises chemical species comprising gadolinium, such as gadolinium chloride ($GdCl_3$). In one embodiment, the at least one magnetic resonance contrast agent is disposed within the carbon microtube. In another embodiment, the at least one magnetic resonance contrast is disposed on a surface of the carbon microtube.

Carbon microtubes, according to some embodiments, can be doped with boron nitrogen, or combinations thereof. In one embodiment, doped carbon microtubes can comprise boron in amount ranging from about 0.01 percent, by weight to about 10 percent, by weight. In another embodiment, doped carbon microtubes can comprise about 5 percent, by weight boron. In other embodiments, doped carbon microtubes can comprise nitrogen in an amount ranging from about 0.01 percent, by weight, to about 30 percent, by weight or from about 5 percent, by weight, to about 25 percent, by weight. In another embodiment, doped carbon microtubes can comprise nitrogen in an amount greater than 30 percent, by weight. In another embodiment, doped carbon microtubes can comprise from about 10 percent, by weight nitrogen to about 20 percent, by weight nitrogen. In a further embodiment, doped carbon microtubes can comprise less than about 1 percent, by weight nitrogen. In some embodiments, doped carbon microtubes can comprise between about 5 percent, by weight and about 10 percent by weight boron and/or nitrogen.

Moreover, in one embodiment, carbon microtubes comprise substantially no iron. In another embodiment, carbon microtubes do not comprise iron.

Carbon nanotubes as well as carbon microtubes, in some embodiments, have at least one surface functionalized with at least one hydrophilic chemical species. Carbon nanotubes having at least one surface functionalized with at least one hydrophilic chemical species, in some embodiments, comprise branched and unbranched carbon nanotubes. Moreover, carbon microtubes having at least one surface functionalized with at least one hydrophilic chemical species, in some embodiments, have bent, curved, and/or folded architectures or structures.

Hydrophilic chemical species suitable for functionalizing at least one surface of a carbon nanotube or carbon microtube, in one embodiment, comprise species having at least one carboxyl group (COOH). In other embodiments, suitable hydrophilic chemical species can comprise hydrophilic polymers such as, but not limited to, poly(dimethyldiallylammonium chloride), polyethylene glycol, alkoxylated polyethylene glycol, or polypropylene glycol.

In some embodiments, at least one surface of a carbon nanotube or a carbon microtube is functionalized by covalently linking a hydrophilic chemical species to the surface. In other embodiments, at least one surface of a carbon nanotube or a carbon microtube is functionalized by forming non-covalent intermolecular interactions with a hydrophilic chemical species, including ionic, dipole-dipole, and/or Van der Waals interactions. In a further embodiment, at least one surface of a carbon nanotube or a carbon microtube is functionalized by forming covalent and non-covalent interactions with one or more hydrophilic chemical species. Functionalization of at least one surface of carbon nanotubes and/or carbon microtubes with hydrophilic chemical species can increase the solubility and/or dispersion of the nanotubes and microtubes in polar solutions or matrices. Polar solutions, in some embodiments, can comprise aqueous based solutions such as saline solutions or buffer solutions. Polar matrices, in some embodiments, can comprise a polymeric gel.

Figure 4:
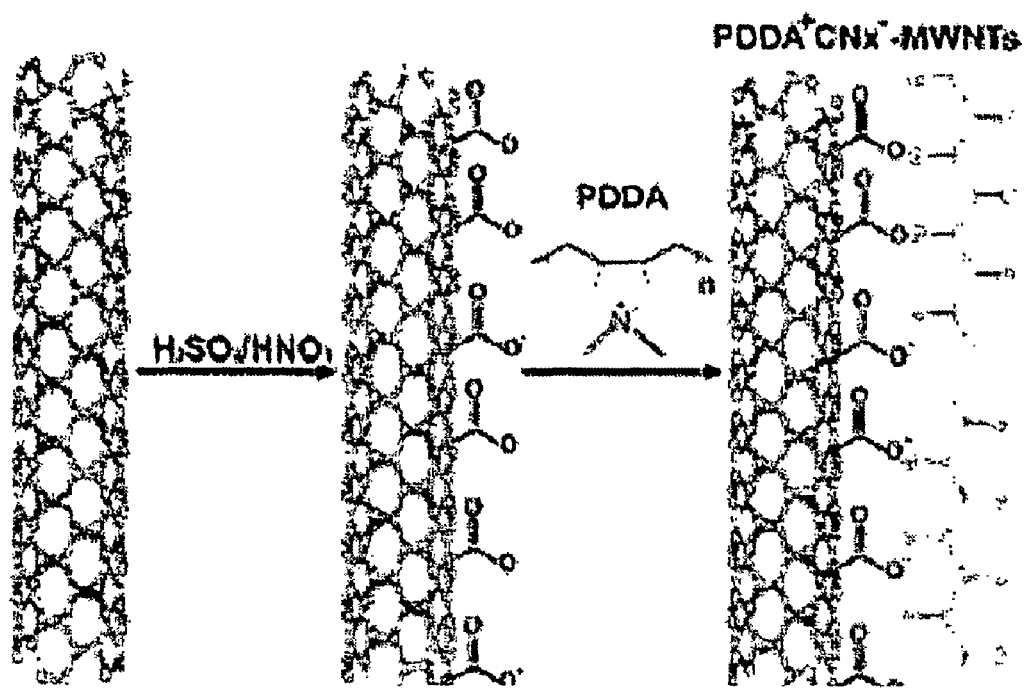
FIG. 4 illustrates surface functionalization of a carbon nanotube according to one embodiment of the present invention.

FIG. 4 illustrates a method of functionalizing a surface of a carbon nanotube with hydrophilic chemical species according to one embodiment of the present invention. The first step in FIG. 4 illustrates functionalization of a carbon nanotube surface by covalently linking a chemical species comprising a carboxyl group to the surface. Covalent linking of a chemical species can be accomplished by acid treatment of the nanotubes followed by 2+2 cycloadditions of the desired groups. The second step of FIG. 4 illustrates electrostatic association of a hydrophilic polymer to the surface of the nanotube through interaction with the carboxyl surface species.

In other embodiments, a carbon nanotube or a carbon microtube comprises a surface functionalized with at least one targeting ligand. "Targeting ligand," as used herein, refers to a ligand or receptor having a specific affinity for a particular chemical species. Moreover, "targeting," as used herein encompasses the use of antibody-antigen binding, ligand-receptor binding, and other chemical binding interactions. In some embodiments, targeting ligands can comprise polyclonal antibodies, monoclonal antibodies, chimeric antibodies, humanized antibodies, recombinant antibodies, bispecific antibodies, antibody fragments, recombinant single chain antibody fragments, aptamers, (ssDNA fragments), and peptides.

Targeting ligands, according to some embodiments of the present invention, can comprise chemokine and cytokine receptors such as CXCR4, CCR7, RANK, Interleukin 1 alpha, Interleukin 1 beta, and Interleukin 2-18; death receptors such as TNF, DR1-5, TRAIL, fas, and lymphotoxin; glucose transporters (Glut1, etc.), Dmt 1, and lipocalin; viral receptors such as HSV receptor, Adenovirus receptor, and EBV receptor; cell surface receptor ligands such as Fas ligand and Wnt; shed receptors and other proteins present in blood such as IGF (insulin-like growth factor), BMP (bone morphogenic protein) antagonists, CA125, tissue factor, tissue plasminogen activator, thryoglobulin, alpha fetoprotein, HCG, H kininogen, L kininogen, and ferritin; cell surface receptors such as DCC (deleted in colorectal cancer), angiotensin receptors, PTCH (human homolog of *Drosophila* patched), RET, Kit, NGF (nerve growth factor) receptor, CGSF, GM-CSF (granulocyte macrophage colony stimulating factor) receptor, transferrin receptor, Frizzled, LRP, and Wise; cell adhesion molecules such as cadherins, CD31 (endothelial cell adhesion molecule), N-CAM (neural cell adhesion molecule), I-CAM (intercellular cell adhesion molecule), integrins, and selectins (E-selectin, P-selectin, L-selectin); receptors for extracellular matrix proteins, such as laminin receptors and fibronectin receptors; growth factor receptors such as FGF, EGF, PDGF, VEGF, FLIT, insulin receptor, IGF, BMP, met (HGF receptor), TGFbeta, and BMP antagonists; cell surface antigens such as CD5, CD44, CD20, CD57, MUC, proteoglycans, PSMA, HER2, and CEA; efflux pumps such as Mdr, Mrp, and Bcrp; and other surface proteins such as uPAR, thrombospondin, MHC molecules, Beta 2 microglobulin, Toll receptors, and a LDL receptor.

Targeting ligands, according to some embodiments, are operable to bind to a cancer marker. In such embodiments, a targeting ligand can be designed to target a specific cancer cell marker or markers. The particular cancer cell marker may be specific to, but not limited to, the type and location of the cancer, such as, for example, tumors, metastatic cancer, minimal residual disease and the like.

The cancer marker or markers may be selected such that they represent a viable target on the cancer cell of interest. Cancer markers, in some embodiments, may be expressed on the surface of cancer cells and not expressed on the surface of healthy cells to permit adequate cellular differentiation. In some embodiments, cancer markers are not readily shed from cellular surfaces. In the event that a cancer marker is shed, according to some embodiments, a targeting ligand may still recognize a particular epitope of the marker that remains on the cellular surface. Alternatively, if a cancer marker is shed, the surface of a nanotube or microtube may comprise one or more additional targeting ligands operable to recognize such shed entities as markers for the cancerous cell.

In another aspect, the present invention provides a nanoparticle composition comprising a spherical or faceted substrate and a plurality of carbon nanotubes coupled to the substrate. In some embodiments, the spherical or faceted substrate can comprise silica. In other embodiments, the substrate may comprise iron.

Figure 5:
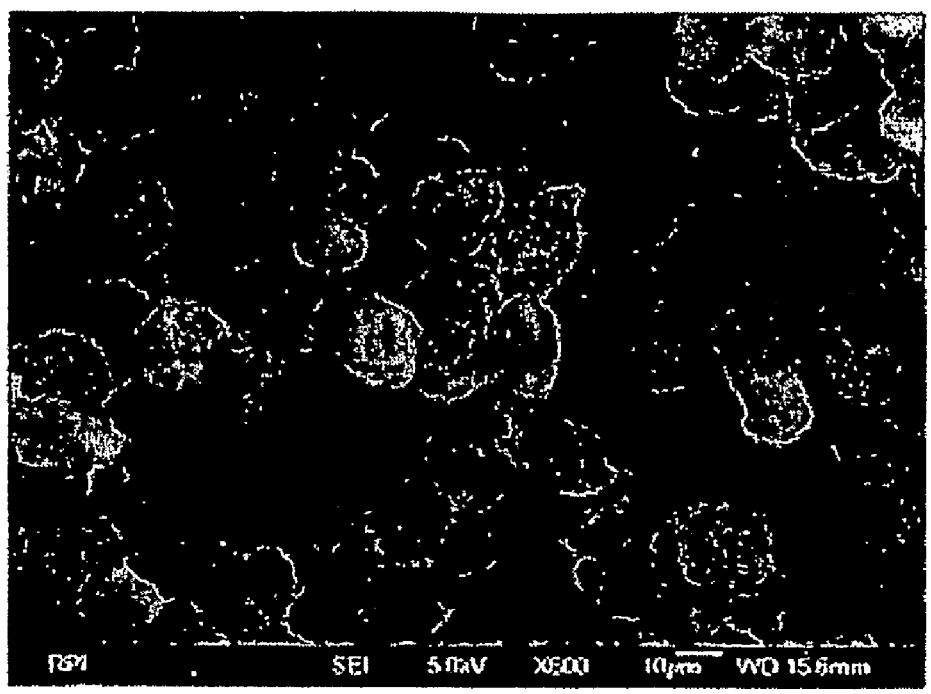
FIG. 5 illustrates carbon nanotubes disposed on a spherical substrate according to one embodiment of the present invention.

Moreover, carbon nanotubes coupled to the spherical or faceted substrate, according to embodiments of the present invention, can comprise carbon nanotubes of any construction consistent with that described herein, including nanotubes comprising iron. FIG. 5 illustrates a nanoparticle composition comprising a spherical silica substrate and a plurality of carbon nanotubes coupled to the substrate according to an embodiment of the present invention.

The present invention also provides methods of producing carbon nanotubes and carbon microtubes. In one embodiment, a method of producing carbon nanotubes or carbon microtubes comprises providing a solution comprising a carbon source and an iron source, injecting the solution into a preheater, vaporizing the solution, transporting the solution to a furnace in a carrier gas, and pyrolyzing the solution. In some embodiments, a carbon source can comprise xylenes. An iron source, according to some embodiments, can comprise ferrocine. Moreover, a suitable carrier gas can comprise hydrogen. In some embodiments, carbon nanotubes and carbon microtubes produced by the foregoing furnace method comprise iron.

Figure 6:
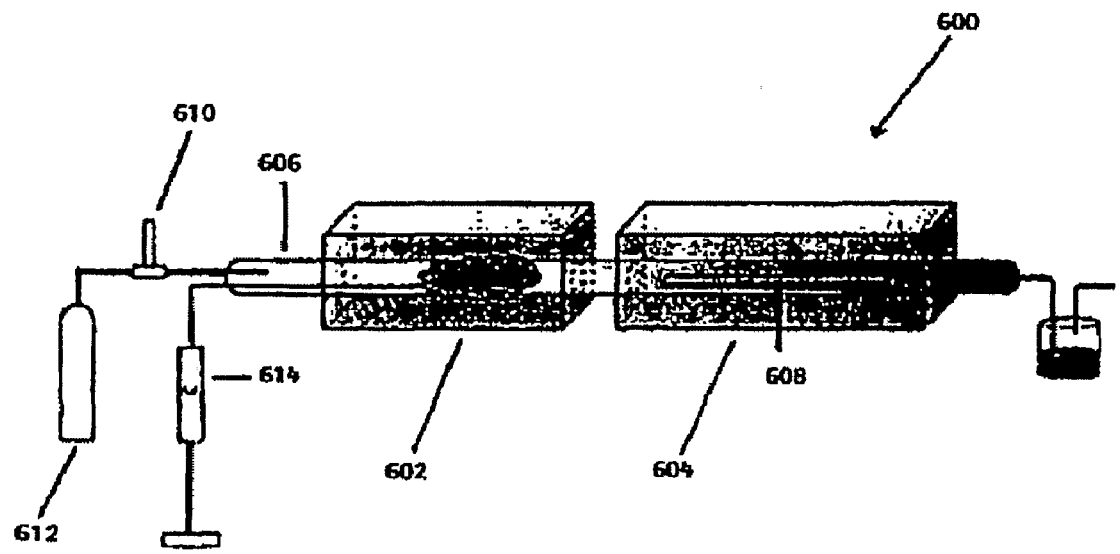
FIG. 6 illustrates carbon nanotube synthesis according to one embodiment of the present invention.

FIG. 6 illustrates a process for producing carbon nanotubes or carbon microtubes comprising iron according to one embodiment of the present invention. A two stage tubular quartz furnace (600) is provided wherein the first stage comprises a preheater (602), and the second stage comprises the growth oven (604). A quartz tube (606) extends through both the preheater (602) and the growth oven (604). In some embodiments, the quartz tube (606) can have a diameter of about 45 mm and an overall length of about 450 mm and has an appropriate substrate (608) for carbon nanotube deposition, such as silica, disposed therein. A carrier gas (612) is connected to the quartz tube through a valve (610) to control the carrier gas flow rate. In some embodiments, the carrier gas can comprise hydrogen and have a flow rate of about 320 sccm. In other embodiments, argon can serve as the carrier gas and have a flow rate of about 40 sccm.

An injection pump (614) is also connected to the quartz tube and is operable to inject a solution comprising a carbon source and an iron source into the quartz tube (606) at a point inside the preheater (602). The solution, in one embodiment, can comprise 0.3 g of ferrocine dissolved in 30 ml of xylene. In some embodiments, the injection pump (614) can inject the solution at a rate of 5 ml/hr. In other embodiments, the injection pump (614) can inject the solution at a rate of 30 ml/hr. In a further embodiment, the injection pump (614) can inject the solution at a rate ranging from 1 ml/hr to 500 ml/hr.

The preheater (602) can be set to a temperature ranging from about of 60° C. to about 250° C. while the growth oven (604) can be set to a temperature ranging from about 600° C. to about 900° C. In some embodiments, the preheater (602) can be set to a temperature ranging from 160° C. to 190° C., and the growth oven (604) can be set to a temperature ranging from about 800° C. to about 900° C.

With the carrier gas (612) flowing at a desired rate, the injection pump (614) injects the desired amount of solution into the quartz tube (606). The solution vaporizes in the preheater and is subsequently carried into the growth oven by the carrier gas for pyrolitic decomposition to produce carbon nanotubes or carbon microtubes on the substrate (608).

In some embodiments, modulating the injection rate of a solution comprising a carbon source and an iron source can vary the intervals at which iron is incorporated into carbon nanotubes and/or carbon microtubes of the present invention. In other embodiments, modulating the flow rate of the carrier gas transporting a vaporized solution comprising a carbon source and an iron source can vary the intervals at which iron is incorporated into carbon nanotubes and/or carbon microtubes of the present invention. In a further embodiment, simultaneously modulating the injection rate of a solution comprising a carbon source and an iron source and the flow rate of a carrier gas transporting the vaporized solution can vary the intervals at which iron is incorporated in carbon nanotubes and/or carbon microtubes of the present invention. As a result, iron can be incorporated into carbon nanotubes and carbon microtubes of the present invention at periodic or non-periodic intervals.

In some embodiments, iron can be incorporated into carbon nanotubes and carbon microtubes at about 25 nm intervals. In other embodiments, iron can be incorporated into carbon nanotubes and carbon microtubes at about 50 nm intervals. In another embodiment, iron can be incorporated into carbon nanotubes and carbon microtubes at about 100 nm intervals. In further embodiments, iron can be incorporated into carbon nanotubes as well as carbon microtubes at about 200 nm or about 500 nm intervals.

In some embodiments of carbon nanotubes or carbon microtubes doped with boron and/or nitrogen, a boron and/or nitrogen source can be added to the solution comprising ferrocine. In one embodiment, for example, pyridine can be placed into solution with ferrocine to produce nitrogen doped carbon nanotubes as well as nitrogen doped carbon microtubes. In other embodiments, a nitrogen source can comprise nitrogen used for imaging by positron emission tomography, such as $^{15}N$. In some embodiments, sources for boron comprise pure boron, boron oxide, and boron nitrides. Alternatively, laser ablated nanotube growth techniques use targets with various boron and nitrogen contents. In some embodiments, the degree of boron and nitrogen doping in a carbon nanotube or microtube can be at least partially tailored by varying the concentration of the boron or nitrogen source in the ferrocine solution.

Carbon nanotubes and carbon microtubes, according to embodiments of the present invention, are operable to absorb electromagnetic energy and subsequently dissipate the absorbed electromagnetic energy as heat into the environment surrounding the nanotubes or microtubes. As a result, carbon nanotubes and carbon microtubes are operable to be used as thermal induction agents.

In some embodiments, carbon nanotubes and carbon microtubes can ablate when irradiated with a sufficient amount of electromagnetic radiation. Carbon nanotube or carbon microtube ablation can occur when the dissipation of electromagnetic radiation as heat becomes so great that the carbon lattice dissociates.

The present invention, according to some embodiments, provides methods of modulating carbon nanotube as well as carbon microtube thermal induction and ablation properties. In one embodiment, a method of modulating carbon nanotube or carbon microtube thermal induction comprises doping carbon nanotubes or carbon microtubes with boron, nitrogen, or combinations thereof. In another embodiment, a method of modulating carbon nanotube or carbon microtube ablation threshold comprises doping carbon nanotubes or carbon microtubes with boron, nitrogen, or combinations thereof.

Figure 7:
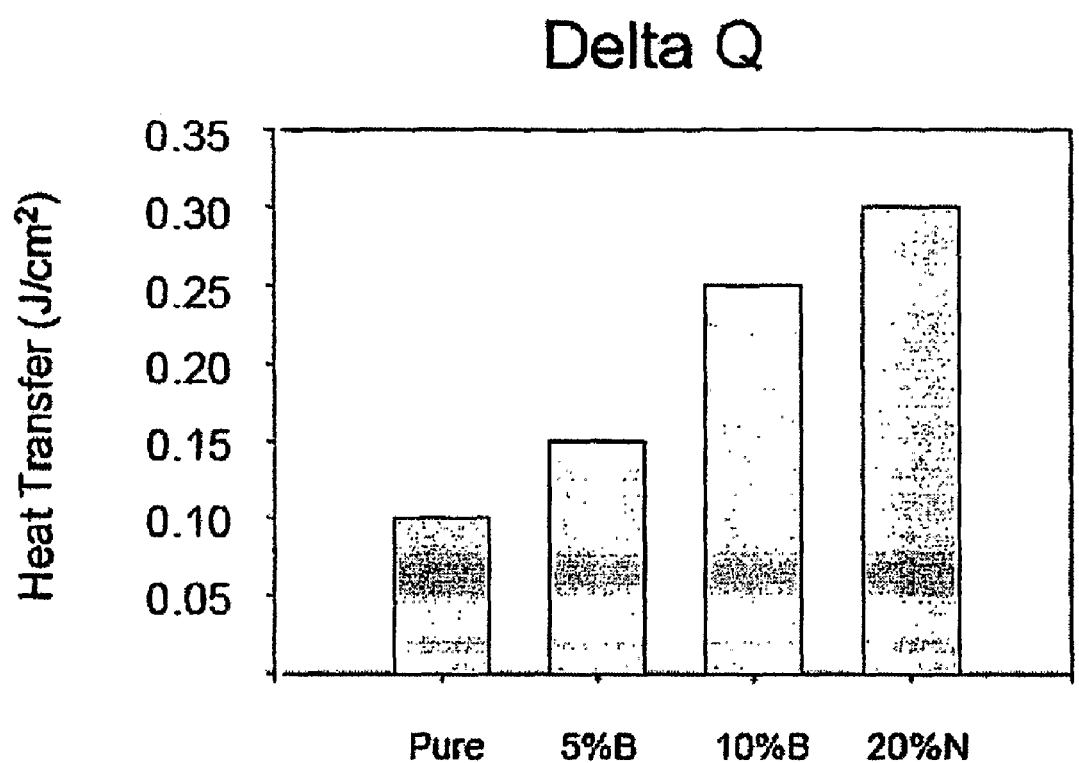
FIG. 7 illustrates heat transfer properties of carbon nanotubes according to embodiments of the present invention.

FIG. 7 illustrates the thermal induction properties of carbon nanotubes doped with various amounts of boron and nitrogen. As displayed in FIG. 7, the amount of heat produced by carbon nanotubes when exposed to electromagnetic radiation increases with higher levels of boron and nitrogen doping.

Figure 8:
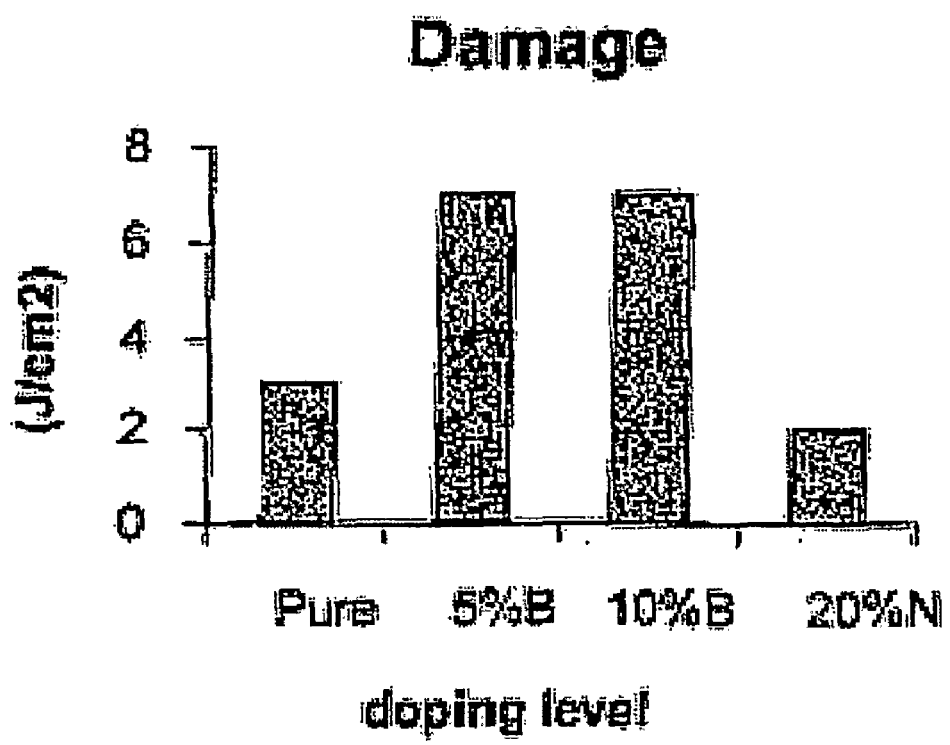
FIG. 8 illustrates carbon nanotube ablation threshold according to embodiments of the present invention.

FIG. 8 illustrates ablation thresholds for carbon nanotubes doped with various amounts of boron and nitrogen. As displayed in FIG. 8, ablation threshold can initially increase with low levels of boron and nitrogen doping. At higher levels of doping, however, the carbon nanotube lattice can become weakened with defects produced by boron and/or nitrogen atoms resulting in lower ablation thresholds.

In view of these effects on thermal induction and ablation threshold, the amount of heat provided by a carbon nanotube or carbon microtube to an environment can be tailored for a specific application.

The present invention additionally provides methods for producing branched carbon nanotubes. In an embodiment, a method for producing branched nanotubes comprises providing an anodized template comprising branched pore structures and synthesizing carbon nanotubes within the branched pore structures. Branched structures, as provided herein, comprise multiple branches, multiple branches with multiple branches, Y branches, Y branches with multiple branches, and multilevel Y branches.

In some embodiments, a method for producing branched nanotubes further comprises electrodepositing at least one metal inside the carbon nanotubes. At least one metal, according to some embodiments, comprises a transition metal, such as iron, nickel, cobalt, copper, or gadolinium.

Providing an anodized template comprising branched pore structures, in one embodiment, comprises a two-step process. In the first step, high purity aluminum foils can be anodized in 0.3 M oxalic acid solution at 8-10° C. under constant voltage (in the range of 40-72 $V_{dc}$) for 8 hours. The formed anodic aluminum can subsequently be removed. In the second step, anodization can proceed under the same conditions as the first step to produce primary stem pores in the anodic aluminum oxide (AAO) template. Subsequent to the production of the stem pores, the anodization voltage can be reduced by a factor of $1/(n)^{0.5}$ to create multiply branched (n branches) pores.

In a further embodiment, the anodization voltage can be further reduced in an additional third step by a factor of $1/(m)^{0.5}$ to generate second generation multibranched pores growing from the first generation (n branches) pores.

Synthesizing carbon nanotubes within the branched pore structures, according to some embodiments, can comprise growing carbon nanotubes by chemical vapor deposition. Growth of carbon nanotubes inside branched pore structures of templates by chemical vapor deposition, in some embodiments, can comprise the pyrolysis of acetylene. In one embodiment, for example, a gaseous mixture of argon (85%) and acetylene (15%) having a flow rate of 35 ml/min can be pyrolyzed inside the pores of an aluminum template at 650° C. for a period of 1-2 hours to produce branched carbon nanotubes.

Synthesis of carbon nanotubes in a porous template can obviate the use of ferrocine in the chemical vapor deposition process. Iron and other metal particles, including other transition metals, can be subsequently disposed inside carbon nanotubes grown in the pores of a template by electrodeposition processes.

In one embodiment, an electrodeposition process can comprise disposing an adhesion layer of titanium having a thickness of about 10 nm to the stem pore side of the porous template. A copper film having a thickness of about 1 µm can be subsequently disposed on the titanium adhesion layer. The adhesion layer and copper film can cover the pores completely and serve as the working electrode in the electrodeposition process. The adhesion layer and copper film can be deposited on the porous template by electron beam evaporation. After formation of the working electrode, metal particles and/or metal nanowires can be disposed in carbon nanotubes of the porous template using standard procedure such as those set forth in (1993) Science 261, pp. 1316-1319 which is hereby incorporated by reference in its entirety.

In some embodiments, a method for producing branched carbon nanotubes further comprises removing the anodized template. Anodized templates can be removed, according to some embodiments of the present invention, by dissolving the template in hydrofluoric acid (20%).

Figure 9:
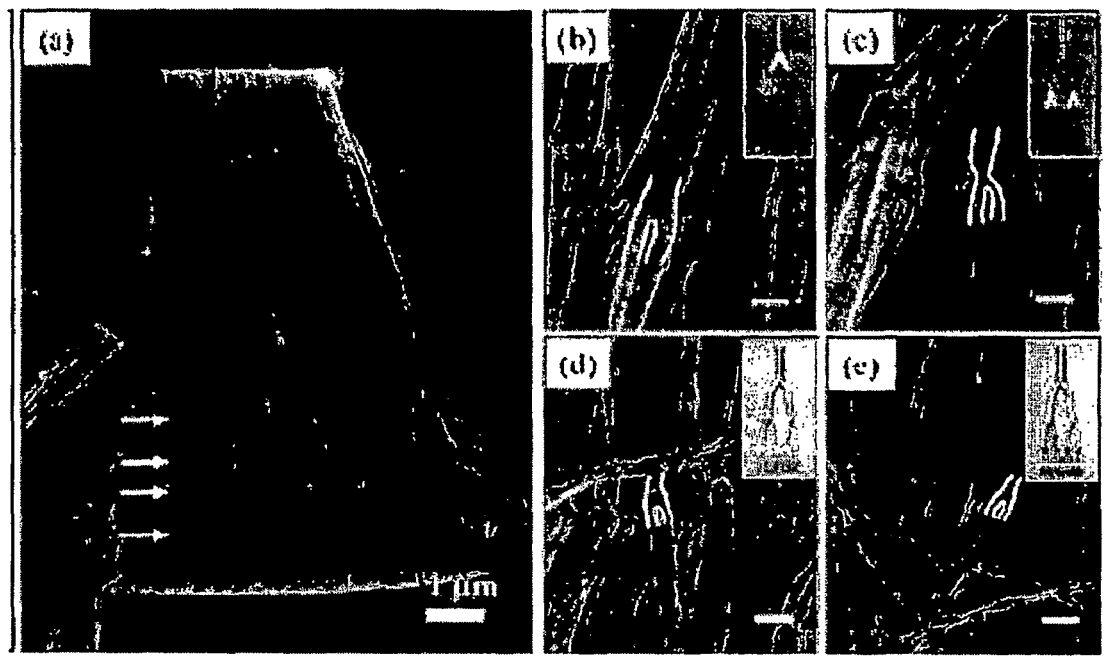
FIG. 9 illustrates branched carbon nanotube architectures according to embodiments of the present invention.

Branched carbon nanotubes produced in accordance with methods of the present invention are provided in FIG. 9.

The present invention also provides systems and methods incorporating carbon nanoparticles and/or carbon microparticles for the treatment of disease. In some embodiments, carbon nanoparticles incorporated into systems and methods for the treatment of disease comprise carbon nanotubes. In some embodiment, carbon microparticles incorporated into systems and methods for the treatment of disease comprise carbon microtubes. In one embodiment, a carbon microtube has a bent, curved, and/or folded structure.

It is contemplated that any of the carbon nanotube or carbon microtube constructions provided hereinabove are suitable for use in systems and methods for the treatment of disease according to various embodiments of the present invention. It is additionally contemplated that the physical and chemical properties of carbon nanotubes and carbon microtubes may be tailored, as provided herein, for particular disease treatment applications.

In an embodiment, the present invention provides a disease treatment system comprising a thermal induction agent and a radiation source, wherein the thermal induction agent comprises at least one carbon nanoparticle, carbon microparticle, or combination thereof. In some embodiments, the at least one carbon nanoparticle comprises a carbon nanotube. In some embodiments, the at least one carbon microparticle comprises a carbon microtube. "Thermal induction agent", in embodiments of the present invention, refers to a chemical species operable to transfer heat energy to its surrounding environment when exposed to electromagnetic radiation. In some embodiments, radiation source comprises an infrared radiation source. An infrared radiation source, in an embodiment, can comprise Nd:YAG laser. In other embodiments, a radiation source comprises a microwave radiation source.

In another embodiment, the present invention provides a disease imaging and treatment system comprising a magnetic field source, a radiation source, and a thermally inducting contrast agent comprising at least one carbon nanoparticle or at least one carbon microparticle, wherein the carbon nanoparticle and/or the carbon microparticle comprises iron. A contrast agent, as used herein, refers to a chemical species operable to alter spin relaxation rates of nuclei surrounding the chemical species, thereby producing contrast in a magnetic resonance image (MRI). The at least one carbon nanoparticle, in some embodiments, comprises a carbon nanotube as provided herein. In some embodiments, carbon nanotubes comprising $^{15}N$ can be used in positron emission tomography and magnetic resonance imaging. The at least one carbon microparticle can comprise a carbon microtube. In one embodiment, a carbon microtube has a bent, curved, and/or folded structure.

In some embodiments, a magnetic field source comprises magnetic field sources used in magnetic resonance imaging applications. Moreover, a radiation source, according to some embodiments, comprises a first radiation source and a second radiation source. A first radiation source can comprise a radio frequency source while a second radiation source can comprise an infrared radiation source or a microwave radiation source.

The present invention also provides methods of treating disease. In one embodiment, a method for treating disease comprises disposing at least one carbon nanoparticle and/or carbon microparticle in a biological environment and heating the biological environment using the nanoparticle or microparticle. In some embodiments, the at least one carbon nanoparticle comprises a carbon nanotube as provided herein. A carbon microparticle, in some embodiments, comprises a carbon microtube. In one embodiment, a carbon microtube has a bent, curved, and/or folded structure.

A biological environment, according to some embodiments, comprises diseased human or animal tissue. In some embodiments, diseased human or animal tissues comprises cancerous tissues such as tumors or tissues otherwise comprising cancerous cells. Tumors, in some embodiments, can comprise "superficial tumors." "Superficial tumors", as used herein, are tumors located in a human or other animal at a depth of less than or equal to about 4 cm. Non-limiting examples of superficial tumors include skin tumors, soft tissue and bone neoplasms (primary and metastatic), kidney tumors, and prostate tumors. In other embodiments, tumors can be located at a depth greater than about 4 cm.

Disposing nanoparticles and/or microparticles in a biological environment, in some embodiments, comprises dispersing carbon nanoparticles and/or carbon microparticles in a physiologically acceptable carrier and introducing the carrier into the biological environment.

Physiologically acceptable carriers, according to some embodiments, comprise solutions or gels compatible with human and/or animal tissue. In some embodiments, physiologically acceptable solutions comprise water, saline solutions and/or buffer solutions. Buffer solutions, in some embodiments, comprise carbonates, phosphates (e.g. phosphate buffered saline), acetates, or organic buffers such as tris(hydroxymethyl)aminoethane (Tris), N-2-hydroxyethylpiperazine-N'-2-ethanesulfonic acid (HEPES), or 3-(N-morpholino)propanesulfonic acid (MOPS). In some embodiments, gels comprise hydrogels, such as those constructed from polyvinyl alcohol, or dextran such as carboxymethyl dextran. In other embodiments, gels comprise hyaluronic acid.

In some embodiments, a physiologically acceptable carrier comprises ethylene oxide and propylene oxide copolymers such as those available from BASF of Florham Park, N.J. under the tradename PLURONIC®. In other embodiments, a physiological acceptable carrier comprises collagen, chitosan, alginates, or combinations thereof. Moreover, physiologically acceptable carriers, in some embodiments, comprise dispersants such as poly(diallyldimethylammonium chloride) (PDDA), surfactants, or combinations thereof. In a further embodiment, a physiologically acceptable carrier comprises poly(lactic)-co-glycolic acid, fibrinogin, chondroitan, or combinations thereof.

In some embodiments, carbon nanoparticles and/or carbon microparticles are disposed in a physiologically acceptable carrier in a therapeutically effective amount. A therapeutically effective amount of carbon nanoparticles and/or microparticles can depend on a several factors including the volume of the diseased tissue to be treated and the type of diseased tissue to be treated. In some embodiments, carbon nanoparticles and/or carbon microparticles are disposed in a physiologically acceptable carrier at a concentration ranging from about 0.1 µg/ml to about 5 mg/ml. In another embodiment, carbon nanoparticles and/or carbon microparticles, are disposed in a physiologically acceptable carrier at a concentration ranging from about 1 µg/ml to about 2 mg/ml, from about 10 µg/ml to about 500 µg/ml, from about 50 µg/ml to about 300 µg/ml, or from about 100 µg/ml to about 200 µg/ml. In a further embodiment, carbon nanoparticles and/or carbon microparticles are disposed in a physiologically acceptable carrier at a concentration greater than about 1 mg/ml or less than about 0.1 µg/ml. In one embodiment, carbon nanoparticles and/or microparticles are disposed in a physiological carrier at a concentration ranging from about 0.5 µg/ml to about 10 µg/ml.

In some embodiments, disposing carbon nanoparticles and/or carbon microparticles in a biological environment comprises injecting the carbon nanoparticles and/or carbon microparticles directly into the biological environment. In one embodiment, for example, a composition comprising carbon nanotubes, carbon microtubes, or mixtures thereof dispersed in a physiologically acceptable carrier is injected directly into a tumor. In some embodiments, the composition is injected into the vasculature of the tumor, and the carbon nanotubes and/or carbon microtubes do not enter into the cancer cells. In some embodiments, the composition is injected into the vasculature of the tumor, and substantially no carbon nanotubes and/or carbon microtubes enter into the cancer cells. Disposing carbon nanoparticles, carbon microparticles, or mixtures thereof in the vasculature of diseased tissue, such as cancerous tissue or a tumor, in some embodiments, does not cut off, substantially inhibit, substantially constrict or clot the blood supply to the diseased tissue.

In other embodiments, disposing carbon nanoparticles and/or microparticles in a biological environment can comprise administering the carbon nanoparticles and/or carbon microparticles at a site remote from the biological environment to be treated. In one such embodiment, carbon nanoparticles and/or carbon microparticles may be injected or otherwise administered to a human or animal at a location remote from the diseased cells or tissues. A solution of carbon nanoparticles, carbon microparticles, or mixtures thereof, for example, may be administered intravenously or intra-arterially. Once administered, the carbon nanoparticles and/or carbon microparticles can be transported through the human or animal body to the site of diseased tissue or cells. In some embodiments, once the carbon nanoparticles and/or carbon microparticles reach the diseased tissue, such as cancerous tissue, the carbon nanoparticles and/or carbon microparticles do not enter into the cells of the diseased tissue and remain in the vasculature of the diseased tissue.

In embodiments wherein carbon nanoparticles comprise carbon nanotubes, the carbon nanotubes can have at least one surface functionalized with a targeting ligand. Moreover, in embodiments wherein carbon microparticles comprise carbon microtubes, the carbon microtubes have at least one surface functionalized with a targeting ligand. Targeting ligands, according to embodiments of the present invention, can allow a carbon nanotube or a carbon microtube to differentiate between healthy and unhealthy tissues or cells when locating a diseased biological environment. In some embodiments, a targeting ligand can permit a nanotube or microtube to bind to the surface of a diseased cell through antibody/antigen or ligand/receptor interactions.

Once disposed in the desired biological environment, the carbon nanoparticles and/or carbon microparticles can be used to heat the biological environment. Heating a biological environment with carbon nanoparticles and/or microparticles, according to some embodiments, can comprise irradiating the carbon nanoparticles and/or carbon microparticles with a radiation source. In embodiments wherein carbon nanoparticles comprise carbon nanotubes, the carbon nanotubes can be irradiated with an infrared radiation source. An infrared radiation source, in some embodiments, can produce radiation ranging from about 700 nm to about 1100 nm. In other embodiments, an infrared radiation source can produce radiation ranging from about 1000 nm to about 1064 nm or from about 1064 nm to about 1100 nm. In embodiments wherein carbon microparticles comprise carbon microtubes, the carbon microtubes can be irradiated with an infrared radiation source or a microwave radiation source.

In one embodiment, heating a biological environment with carbon nanoparticles, carbon microparticles, or mixtures thereof induces hyperthermia in cells in the biological environment. In one embodiment, for example, carbon nanotubes, carbon microtubes, or mixtures thereof are disposed in the vasculature of a tumor. The nanotubes, microtubes, or mixtures thereof are subsequently irradiated with infrared radiation, microwave radiation, or combinations thereof to heat the tumor cells, thereby inducing hyperthermia in the tumor cells. Inducing hyperthermia in the tumor cells results in the death of the tumor cells.

In some embodiments, a method of the present invention comprising heating a biological environment comprising diseased tissue with one or a plurality of carbon nanoparticles and/or carbon microparticles results in at least a 10% reduction in the volume of the diseased tissue. In other embodiments, a method of the present invention comprising heating a biological environment with one or a plurality of carbon nanoparticles and/or carbon microparticles results in at least a 25% reduction, at least a 50% reduction, at least an 80% reduction, or at least a 90% reduction in the volume of the diseased tissue. In a further embodiment, a method of the present invention comprising heating a biological environment comprising diseased tissue with one or a plurality of carbon nanoparticles and/or carbon microparticles results in substantially complete or complete destruction or elimination of the diseased tissue. In one embodiment, a method of the present invention comprising heating a biological environment comprising diseased tissue with one or a plurality of carbon nanoparticles and/or carbon microparticles results in precluding further growth of the diseased tissue or results in retarding the growth of the diseased tissue.

In some embodiments, the foregoing reductions in the volume of diseased tissue are achieved by application of a single carbon nanoparticle and/or carbon microparticle composition to the diseased tissue followed by a single application of electromagnetic radiation to the composition. In other embodiments, the foregoing reductions in the volume of diseased tissue are achieved by a plurality of applications of electromagnetic radiation to the single carbon nanoparticle and/or carbon microparticle composition. In a further embodiment, the foregoing reductions in the volume of diseased tissue are achieved by application of a plurality of carbon nanoparticle and/or carbon microparticle compositions to the diseased tissue followed by a single application or a plurality of applications of electromagnetic radiation to the compositions.

In some embodiments, the carbon nanotubes and/or carbon microtubes are ablated by the irradiation. The nanotube and/or microtube fragments are subsequently cleared from the surrounding tissue.

When the biological environment comprises a superficial tumor, for example, the superficial tumor can be heated by irradiating the carbon nanotubes and/or carbon microtubes disposed therein with an external radiation source. The close proximity of the superficial tumor to the skin surface of a human or animal can preclude or minimize substantial amounts of radiation absorption by overlying and/or surrounding tissue, thereby permitting the use of an external radiation source.

In some embodiments wherein a tumor or other diseased tissue is located at a greater depth, fiber optics or similar devices can be used endoscopically to penetrate surrounding tissue and deliver radiation to carbon nanotubes and/or carbon microtubes dispersed in an around the diseased tissue. In other embodiments, many external beams of radiation having different incident angles can be focused on a tumor or diseased tissue having a depth greater than that of a superficial tumor. The large number of beams focused on the same region can compensate for the absorption of the radiation by overlying and/or surrounding tissue. Apparatus for providing numerous beams of radiation can comprise GAMMA KNIFE® apparatus available from Elekta Corporation of Stockholm, Sweden or similar multibeam focusing devices.

As provided herein, a feature of the present invention is that carbon nanotubes, carbon microtubes, or mixtures thereof, according to some embodiments, may be utilized in a therapeutic imaging, irradiation and/or ablation method from a location outside the cell wall of the targeted cell. In some embodiments, a carbon nanotube will be located proximate to the cell wall in a therapeutic method.

Carbon nanotubes, according to some embodiments of the present invention, can absorb infrared radiation ranging from about 700 nm to about 1100 nm, from about 3 µm to about 5 µm, or from about 10 µm to about 12 µm. After absorbing infrared radiation, carbon nanotubes can dissipate the absorbed electromagnetic energy in the form of heat energy. The heat produced can be transferred into the biological environment surrounding the carbon nanotubes.

Carbon microtubes, according to some embodiments of the present invention, can absorb infrared radiation ranging from about 700 nm to about 1100 nm, from about 3 µm to about 5 µm, from about 10 µm to about 12 µm or microwave radiation. In some embodiments, microwave radiation has a wavelength ranging from about 1 cm to about 15 cm. After absorbing electromagnetic radiation, carbon nanotubes and carbon microtubes can dissipate the absorbed electromagnetic energy in the form of heat energy. The heat produced can be transferred into the biological environment surrounding the carbon nanotubes and/or carbon microtubes.

In some embodiments, carbon nanoparticles and carbon microparticles are ablated when irradiated. In embodiments wherein the carbon nanoparticles comprise carbon nanotubes, the carbon nanotubes can ablate when irradiated with a sufficient amount infrared radiation. Carbon nanotube ablation can occur when the dissipation of electromagnetic energy as heat becomes so great that the carbon lattice dissociates. In some embodiments, a carbon nanotube lattice dissociates into smaller segments or fragments facilitating removal of the ablated nanotube from a biological environment. Carbon microtubes, in some embodiments, can ablate when irradiated with sufficient amounts of infrared and/or microwave radiation.

In some embodiments, the heat produced by carbon nanoparticles and/or carbon microparticles is sufficient to destroy cells in biological environments surrounding the nanoparticles and/or microparticles. In one embodiment, the heat produced upon irradiating carbon nanotubes and/or carbon microtubes with radiation is sufficient to destroy cancer cells. In other embodiments, the heat produced from irradiated carbon nanotubes and/or carbon microtubes is sufficient to destroy other diseased cells, such as cells infected with viruses like HIV.

Moreover, carbon nanotubes and/or carbon microtubes having at least one surface functionalized with a targeting ligand, in some embodiments, can provide differentiation between diseased cells and tissues and healthy cells and tissues. The differentiation provided by targeting ligands provides methods for the selective destruction of diseased cells and tissues. In some embodiments, a targeting ligand can permit a carbon nanotube or a carbon microtube to bind to the surface of a diseased cell through antibody/antigen or ligand/receptor interactions.

In another embodiment, the present invention provides a method for imaging and treating disease comprising disposing at least one carbon nanoparticle comprising iron or at least one carbon microparticle comprising iron in a biological environment, imaging the biological environment with the carbon nanoparticle or the carbon microparticle, and heating the biological environment with the carbon nanoparticle or the carbon microparticle. In some embodiments, the carbon nanoparticle comprises a carbon nanotube as provided herein. Moreover, in some embodiments, the carbon microparticle comprises a carbon microtube as provided herein.

Disposing at least one carbon nanoparticle or at least one carbon microparticle in a biological environment and heating the biological environment with the carbon nanoparticle or carbon microparticle can be accomplished in accordance with the embodiments set forth above.

Imaging a biological environment using a carbon nanoparticle comprising iron or a carbon microparticle comprising iron, in some embodiments, can comprise inducing a magnetic field, disposing the biological environment comprising the carbon nanoparticle or the carbon microparticle in the induced magnetic field, and irradiating the biological environment with a radio frequency.

Magnetic fields, according to some embodiments of the present invention, can be induced with apparatus typically used in magnetic resonance imaging (MRI) applications. Moreover, radio frequency sources typically used in MRI applications, in some embodiments, can be used to irradiate the biological environment comprising the at least one carbon nanoparticle.

Carbon nanoparticles, including carbon nanotubes, comprising iron can act as contrast agents in MRI imaging applications according to some embodiments. A carbon nanoparticle comprising iron can alter spin relaxation rates of nuclei surrounding the nanoparticle thereby providing contrast in a magnetic resonance image.

Carbon microparticles, including carbon microtubes, comprising iron can act as contrast agents in MRI imaging applications according to some embodiments. A carbon microparticle comprising iron can alter spin relaxation rates of nuclei surrounding the microparticle thereby providing contrast in a magnetic resonance image.

In some embodiments, a surface of a carbon nanotube or a carbon microtube comprising iron can be functionalized with a chelate comprising a transition metal. Transition metal chelates, in some embodiments, can enhance the contrast properties of carbon nanotubes and carbon microtubes in magnetic resonance imaging applications.

In one embodiment, a metal chelate comprises manganese, iron, cobalt, nickel, or gadolinium. Metal chelates, in embodiments of the present invention, comprise at least one organic ligand. Chelating organic ligands, according to some embodiments, can comprise 1,4,7-triaacylononae-N—N'—N''-triacetate, 1,4,7,10-tetrazacyclododecane-N,N',N'',N'''-tertraacetate, or 1,5,9-triazacyclododecane-N,N',N''-triacetate.

In some embodiments, carbon nanotubes and/or carbon microtubes comprising iron can have a surface functionalized with at least one targeting ligand. Carbon nanotubes and/or carbon microtubes comprising iron and having a surface functionalized with at least one targeting ligand, in some embodiments, can be used to identify and image specific cells or tissues. In some embodiments, the cells or tissues imaged comprise diseased cells and tissues. Diseased cells and tissues, in some embodiments, can comprise cancer cells and cancerous tissues, such as tumors. Moreover, once imaged, the carbon nanotubes and/or carbon microtubes can be irradiated with infrared radiation to selectively destroy the diseased cells and tissues.

The present invention also provides pharmaceutical compositions and methods of administering pharmaceutical compositions for the treatment of disease. In one embodiment, the present invention provides a composition comprising a pharmaceutical composition disposed in a casing, the casing comprising a composite material. In some embodiments, the composite casing material comprises plurality of carbon nanoparticles and/or carbon microparticles dispersed in a matrix comprising poly(diallyldimethylammonium) (PDDA) and/or salt thereof. In some embodiments, the carbon nanoparticles comprise carbon nanotubes as provided herein. In some embodiment, the carbon microparticles comprise carbon microtubes as provided herein. In other embodiments, the carbon nanoparticles comprise fullerenes ($C_{60}$). In a further embodiment, the carbon nanoparticles can comprise carbon nanowhiskers. Carbon nanowhiskers, in some embodiments, can comprise a plurality of fullerenes or nanotubes coupled by photo polymerization processes.

A method for administering a pharmaceutical composition, according to some embodiments, can comprise administering a pharmaceutical composition disposed in a casing to an individual and ablating the casing to at least partially release the pharmaceutical composition. In some embodiments, the casing comprises a composite material comprising a plurality of carbon nanoparticles and/or carbon microparticles dispersed in a PDDA matrix.

In embodiments wherein the casing comprises a carbon nanotube-PDDA composite or a carbon microtube-PDDA composite, ablating the casing can comprise irradiating the casing with infrared radiation and/or microwave radiation. In some embodiments, irradiating a composite casing can cause the carbon nanotubes or carbon microtubes to ablate thereby rupturing the casing to at least partially release the pharmaceutical composition disposed therein. Pharmaceutical compositions for use in compositions and methods described herein can comprise chemical species useful for the treatment of cancer and other diseases, such as HIV/AIDS.

The present invention will now illustrated by the following non-limiting examples.

EXAMPLE 1

Synthesis of Carbon Nanotubes Comprising Iron

Nitrogen doped multi-walled carbon nanotubes comprising iron were synthesized in large scale using injection based chemical vapor deposition (CVD) of ferrocine in pyridine. The synthesis of the multi-walled carbon nanotubes was executed in a two-stage quartz furnace (diameter ~45 mm, work length ~450 mm) similar to that illustrated in FIG. 6. Hydrogen was used as the carrier gas with a flow rate of 320 sscm, and the preheater of the two-stage furnace was maintained at 160° C. About 2.7 percent of ferrocine, by weight was dissolved in pyridine, and the resulting solution was injected into the preheater at a rate of 5 ml/hr. The temperature of the furnace ranged from 600° C. to 900° C., and the growth time was set to one hour.

Figure 10:
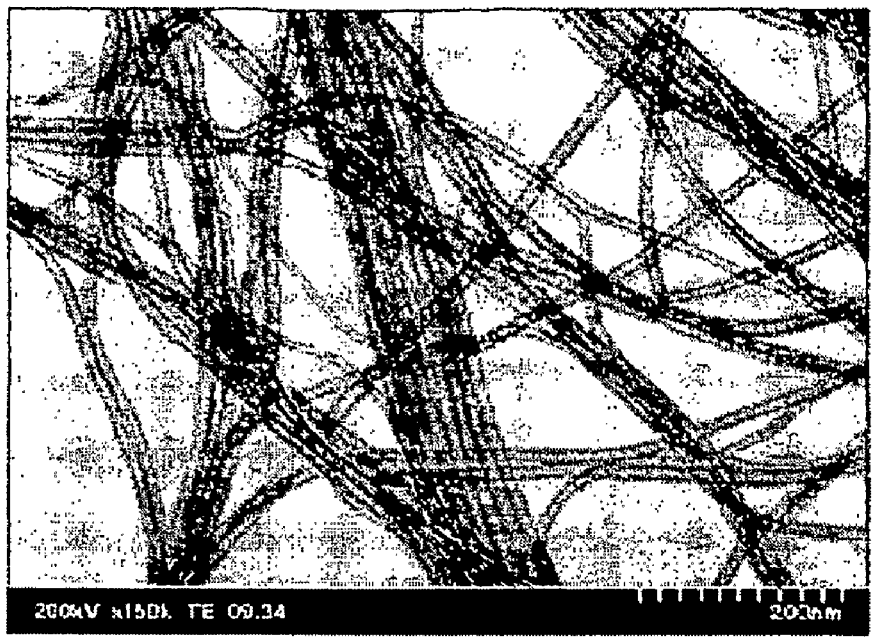
FIG. 10 displays a transmission electron microscopy image of carbon nanotubes according to one embodiment of the present invention.
Figure 11:
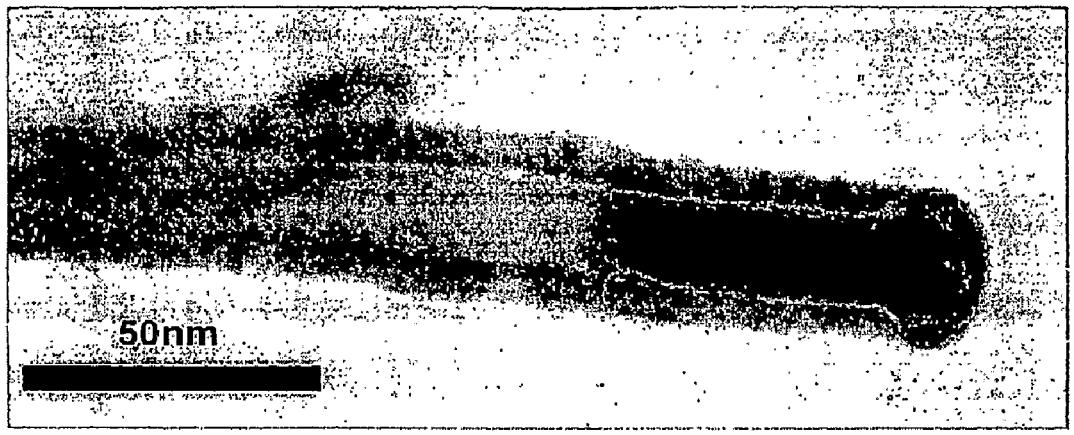
FIG. 11 displays a transmission electron microscopy image of a carbon nanotube according to one embodiment of the present invention.

Analysis of the product by transmission electron spectroscopy (TEM) and scanning tunneling spectroscopy (STS) revealed highly aligned, uniform multi-walled carbon nanotubes having an average diameter of 20 nm. FIG. 10 is a TEM image of carbon nanotubes synthesized at 700° C. in accordance with the parameters set forth in the present example. Moreover, iron was present in the multi-walled nanotubes as shown in the TEM image of FIG. 11.

EXAMPLE 2

Carbon Nanotubes as Magnetic Resonance Imaging (MRI) Contrast Agents

In order to test the MRI contrast abilities of carbon nanotubes comprising iron, according to embodiments of the present invention, carbon nanotubes as produced in Example 1 were mixed with 5E⁶ CRL 1932 cultured kidney cancer cells and imaged using a General Electric (GE) 1.5 T Signal Scanner with Twin Speed gradients (General Electric Healthcare Systems, Milwaukee, Wis.) with the quadrature head coil. An inversion recovery spin echo pulse sequence was modified to acquire 1-dimensional image of the cells at a range of inversion times ranging from 50 milliseconds (ms) to 10 seconds in equally spaced increments. A 30 second repetition time was used to allow the spins to return thermal equilibrium before each excitation. Cultured kidney cancer cells in a solution without carbon nanotubes were used as a control.

The raw magnetic resonance data from the longest inversion time (TI=10 seconds) was subtracted from other raw magnetic resonance data to account for the change in sign of the data. This subtraction allowed T1 to be measured by fitting the data to a three parameter decaying exponential model. The T1 of the control cells was 1747 ms while the T1 of the cells mixed with carbon nanotubes comprising iron was 730 ms. The reduction in T1 illustrates the magnetic resonance contrasting abilities of carbon nanotubes comprising iron.

EXAMPLE 3

Inducement of Cell Death with Carbon Microtubes

In order to test the ability to induce death of diseased cells, multi-walled carbon microtubes having a diameter ranging from about 20-30 nm and a length of about 1.2 µm were suspended in HEPES-buffered saline and sonicated. 50 µl of the suspension was added to one chamber of a dual-chamber cover glass slide containing 3×10⁵ CRL 1932 kidney cancer cells. The other chamber contained cancer cells without addition of the carbon microtube solution. The cells were allowed to incubate for 6 hours at 37° C. in a humidified atmosphere containing 5% $CO_2$.

The cells were subsequently exposed to 3 watts of 1024 nm radiation from a YAG laser for increasing intervals of time ranging from 30 seconds to 240 seconds. The irradiated cells were immediately washed with PBS and stained with calcein AM at 37° C. for 5 minutes. The vital dye stains living cells and is not retained in dead cells. Cells were visualized using a Zeiss LSM 510 Confocal Microscope and excitation with an argon laser.

Figure 12:
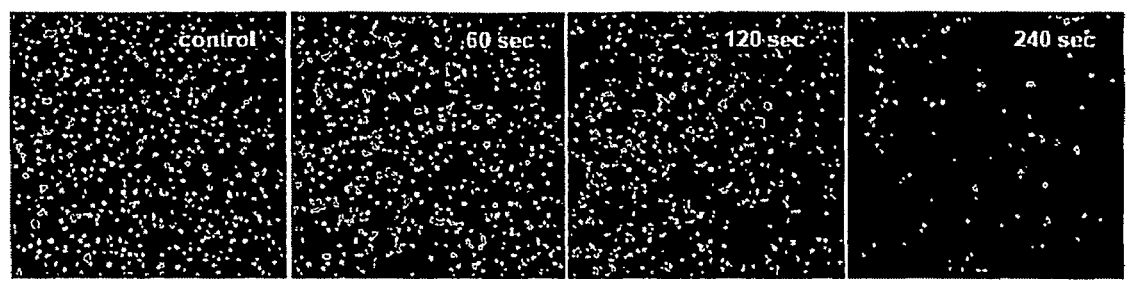
FIG. 12 illustrates carbon microtube induced cell death according to one embodiment of the present invention.

As shown in FIG. 12, the carbon microtubes induced cancer cell death when irradiated with infrared radiation. Moreover, an irradiation time period of 240 seconds induced death in a significant number of the cancer cells. Time periods of irradiation can be tailored, according to embodiments of the present invention, to maximize number of diseased cells destroyed.

Viability prior to light treatment was identical in both chambers indicating that simple coincubation of cells with microtubes did not affect cell survival.

EXAMPLE 4

Synthesis of Carbon Microtubes Having a Mean Length of 1.1 µm

Figure 13:
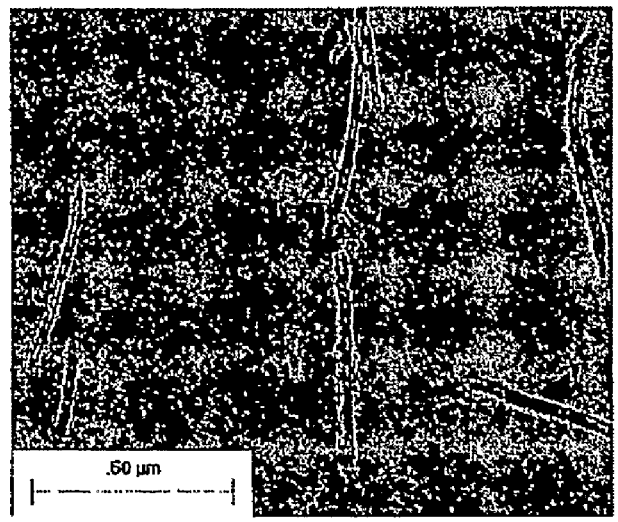
FIG. 13 illustrates carbon microtubes produced according to one embodiment of the present invention.
Figure 14:
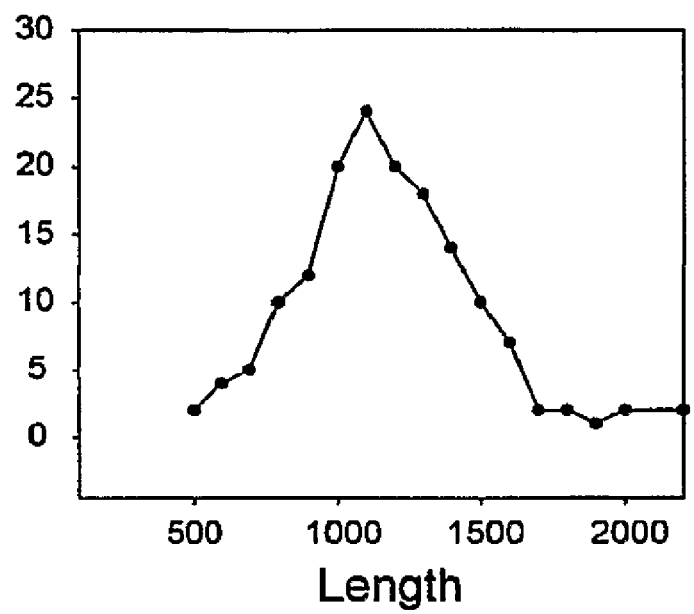
FIG. 14 illustrates carbon microtube length distribution according to one embodiment of the present invention.

Multi-walled carbon microtubes were synthesized in accordance with the procedure set forth in Example 1. X-ray photoelectron spectroscopy (XPS) was used to determine the overall nitrogen concentration of the multi-walled carbon microtubes, which was measured to be from about 1% to about 2% weight percent. Subsequent to formation, the multi-walled carbon microtubes were ultrasonicated in a mixture of concentrated sulfuric acid and nitric acid (3:1) for a period of 7 hours. After extensive washing an drying, the purity and length of the multi-walled carbon microtubes were examined using a Phillips 400 transmission electron (TEM) microscope operating at 80 keV. The examination provided evidence of high purity multi-walled carbon microtubes with almost no catalytic or carbonaceous particles on the surfaces of the carbon nanotubes. FIG. 13 illustrates a TEM image of the produced multi-walled carbon microtubes. Moreover, the multi-walled carbon microtubes displayed a mean length of 1.1 µm. The carbon microtube length distribution is illustrated in FIG. 14. The multi-walled carbon microtubes displayed a diameter of about 15 nm.

EXAMPLE 5

Synthesis of Carbon Nanotubes Having a Mean Length of 700 nm

Figure 15:
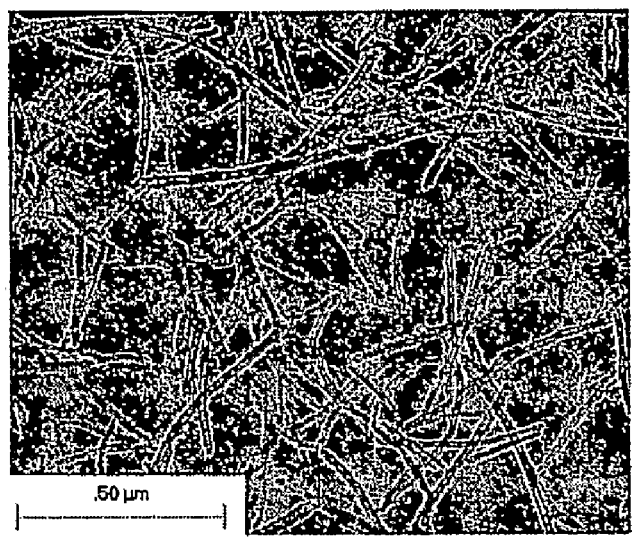
FIG. 15 illustrates carbon nanotubes produced according to one embodiment of the present invention.
Figure 16:
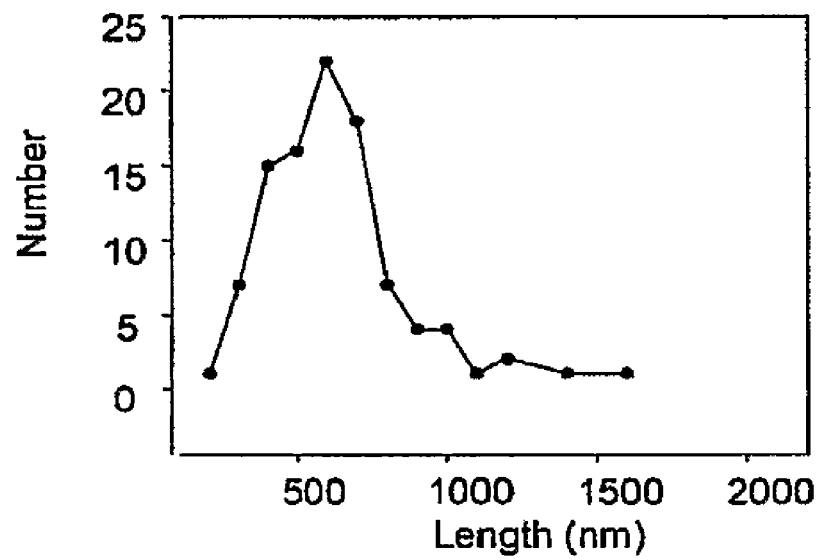
FIG. 16 illustrates carbon nanotube length distribution according to one embodiment of the present invention.

Multi-walled carbon nanotubes were synthesized in accordance with the procedure set forth in Example 1. X-ray photoelectron spectroscopy (XPS) was used to determine the overall nitrogen concentration of the multi-walled carbon nanotubes, which was measured to be from about 1% to about 2% weight percent. Subsequent to formation, the multi-walled carbon nanotubes were ultrasonicated in a mixture of concentrated sulfuric acid and nitric acid (3:1) for a period of 24 hours. After extensive washing an drying, the purity and length of the multi-walled carbon nanotubes were examined using a Phillips 400 transmission electron (TEM) microscope operating at 80 keV. The examination provided evidence of high purity multi-walled carbon nanotubes with almost no catalytic or carbonaceous particles on the surfaces of the carbon nanotubes. FIG. 15 illustrates a TEM image of the produced multi-walled carbon nanotubes. Moreover, the multi-walled carbon nanotubes displayed a mean length of 700 nm. The carbon nanotube length distribution is illustrated in FIG. 16. The multi-walled carbon nanotubes displayed a diameter of about 15 nm.

EXAMPLE 6

Cellular Cytotoxicity Study of Multi-Walled Carbon Microtubes

Figure 17:
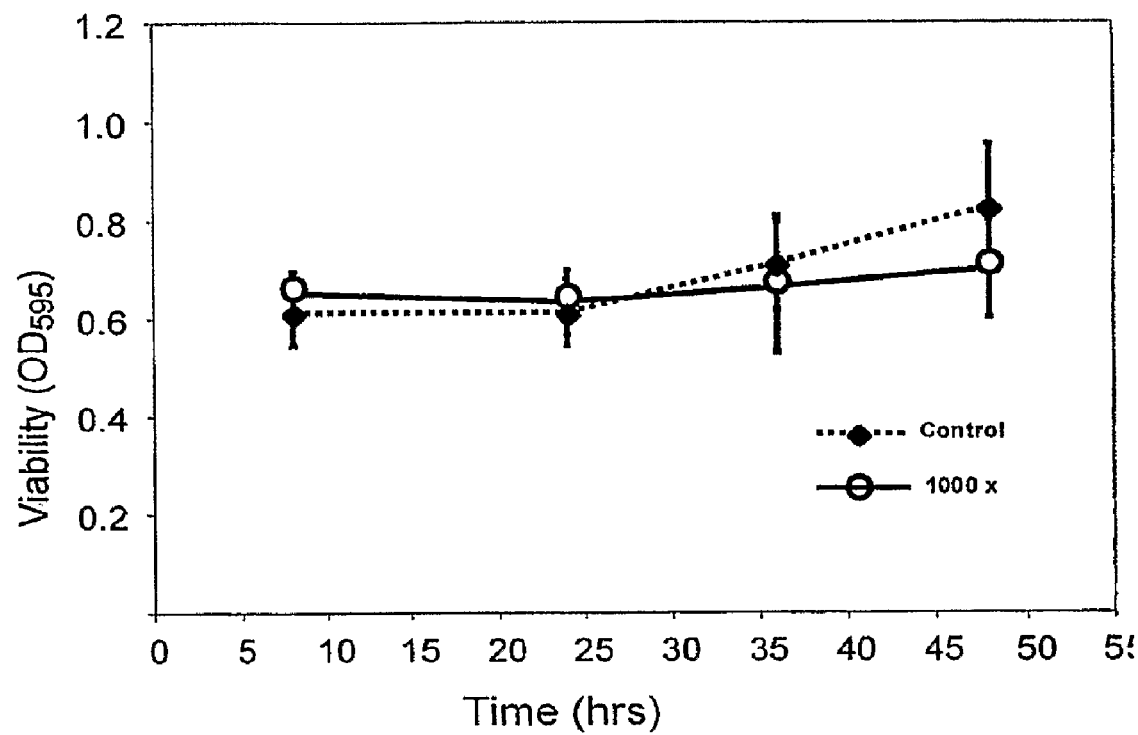
FIG. 17 illustrates cellular viability as a function of mixing with carbon microtubes according to one embodiment of the present invention.

Multi-walled carbon microtubes having an mean length of 1.1 µm were produced in accordance with the procedure described in Example 4. CRL 1932 cancer cells were obtained from the American Type Culture Collection and cultured at 37° C. in a humidifier chamber containing 5% $CO_2$ in McCoy's 5A media supplemented with 10% fetal bovine serum (FBS) and 1% penicillin-streptomycin. Cells were seeded at 1.5×10⁴ cells/well in 48 well culture dishes. 0.1 ml of multi-walled carbon nanotubes suspended in HBS were mixed with 0.9 ml CRL 1932 cancer cells in McCoy's 5A modified media. The ratio of multi-walled microtubes to cells was 1000:1. As demonstrated in FIG. 17, the microtubes produced no discernable effect on cell viability assessed over 48 hours, leading to the conclusion that the multi-walled carbon microtubes are not inherently toxic.

EXAMPLE 7

Effect of Nanotube Concentration on Environment Heating

Figure 18:
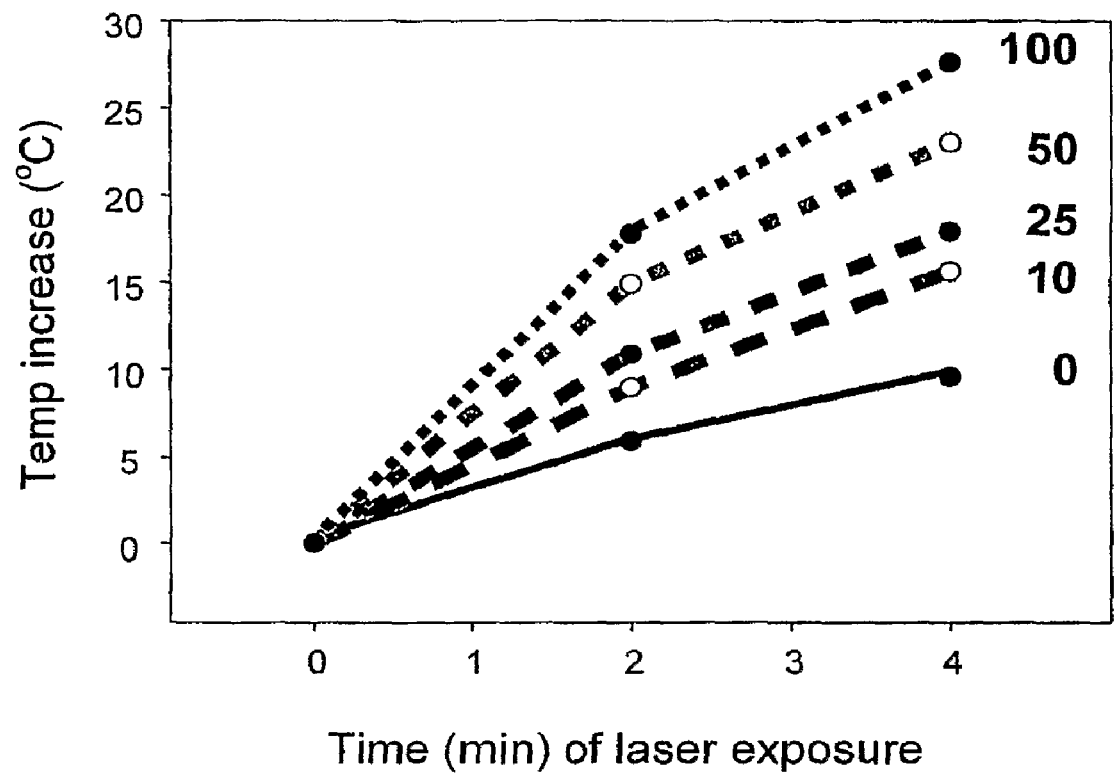
FIG. 18 illustrates carbon nanotube heating of a surrounding environment according to one embodiment of the present invention.

Multi-walled carbon nanotubes having an mean length of 700 nm were produced in accordance with the procedure described in Example 5. A concentration of $1000 \times 10^5$ multi-walled nanotubes/unit volume was designated as an aqueous solution concentration of 100%. This concentration was subsequently diluted to produce additional aqueous solutions of $500 \times 10^5$, $250 \times 10^5$, and $10 \times 10^5$ nanotubes/unit volume representing concentrations of 50%, 25%, and 10% respectively. Each aqueous solution concentration was irradiated with a NIR CW-YAG laser operating at a wavelength of 1064 nm and a laser power of 3 $W/cm^2$ for a time period of up to 4 minutes. As demonstrated in FIG. 18, an increase in temperature of each aqueous solution was registered upon irradiation. The concentration of 100% ($1000 \times 10^5$ multi-walled nanotbes/unit volume) attained the highest temperature increase with each successive concentration drop following in order.

EXAMPLE 8

Cell Viability Following Carbon Microtube Induced Hyperthermia

Multi-walled carbon microtubes having a mean length of 1.1 μm were produced in accordance with Example 4. CRL 1932 cancer cells were obtained from the American Type Culture Collection and cultured at 37° C. in a humidifier chamber containing 5% $CO_2$ in McCoy's 5A media supplemented with 10% fetal bovine serum (FBS) and 1% penicillin-streptomycin. Various concentrations of the 1.1 μm multi-walled carbon microtubes suspended in HBS were incubated with the cancer cells. Cancer cells were incubated at microtube:cell ratios of 1:1, 100:1, and 1000:1. The cultures comprising various carbon microtube:cell ratios were irradiated with a NIR CW-YAG laser operating at a wavelength of 1064 nm and a laser power of 3 $W/cm^2$ for a time period of 4 minutes. Control cells were incubated with the multi-walled carbon microtubes but were not irradiated with the NIR laser or were irradiated with the laser in the absence of microtubes.

Figure 19:
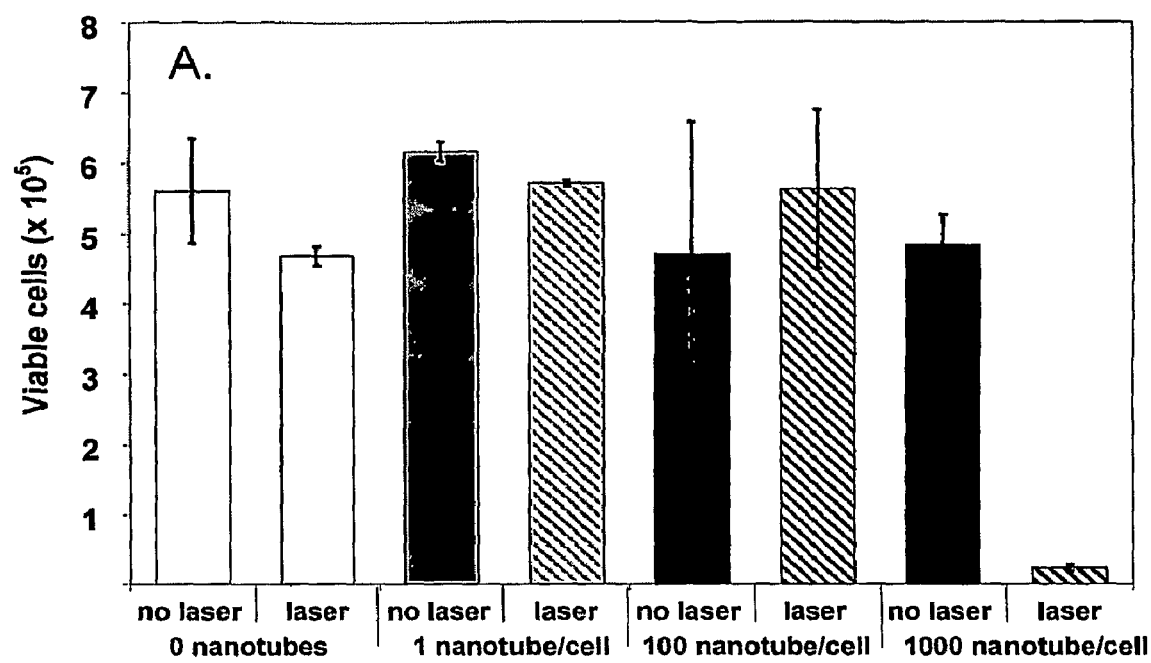
FIG. 19 illustrates cellular viability as a function of carbon microtube concentration when exposed to near infrared radiation (NIR) according to one embodiment of the present invention.
Figure 20:
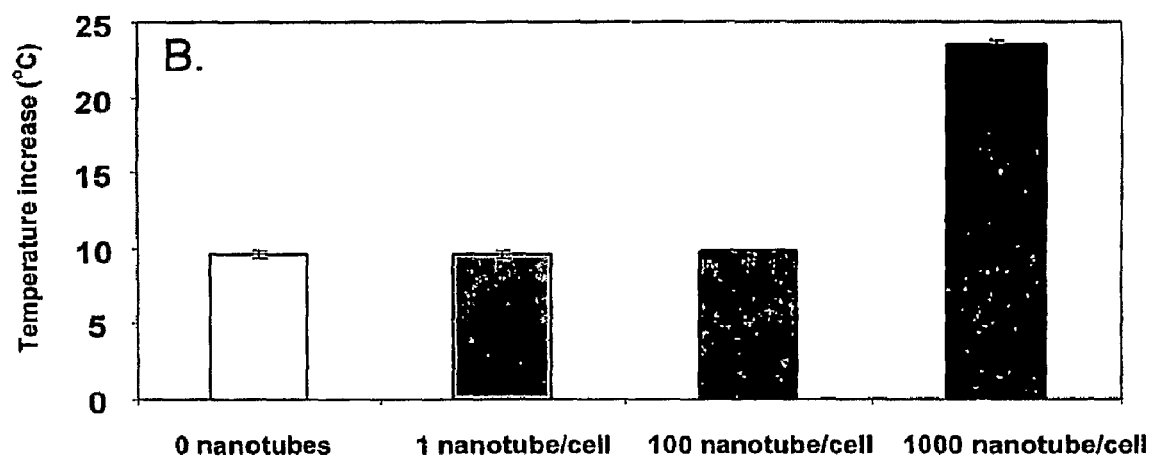
FIG. 20 illustrates temperature increase in a surrounding environment as a function of carbon microtube concentration according to one embodiment of the present invention.

Viability was assessed in all cultures. As illustrated in FIG. 19, in the absence of the 1.1 μm multi-walled carbon microtubes, treatment with NIR laser had no effect on cell viability. As a result, cells display a high transparency to NIR light, and neither exposure to NIR alone nor exposure to microtubes alone is sufficient to induce cell death. Cells incubated with the 1.1 μm multi-walled carbon microtubes and subsequently exposed to NIR demonstrated dramatic dose-dependent decreased in viability, with over 90% cell death at the highest dose tested (e.g. 1000:1). Moreover, the greatest decrease in viability was associated with the greatest increase in temperature. The average number of cells in the 1000:1 microtube/cell sample decreased by $4.62 \times 10^5 +/- 0.47 \times 10^5$ after exposure to the laser wherein a temperature of 57.7+/−1.5° C. was attained. FIG. 20 illustrates that the greatest temperature increase occurred at a 1000:1 microtube:cell ratio.

EXAMPLE 9

Cell Viability Following Carbon Nanotube Induced Hyperthermia

Multi-walled carbon nanotubes having a mean length of 700 nm were produced in accordance with Example 5. CRL 1932 cancer cells were obtained from the American Type Culture Collection and cultured at 37° C. in a humidifier chamber containing 5% $CO_2$ in McCoy's 5A media supplemented with 10% fetal bovine serum (FBS) and 1% penicillin-streptomycin. Various concentrations of the 700 nm multi-walled carbon nanotubes suspended in HBS were incubated with the cancer cells. Cancer cells were incubated at nanotube:cell ratios of 1:1, 1:100, and 1:1000. The cultures comprising carbon nanotube:cell ratios were irradiated with a NIR CW-YAG laser operating at a wavelength of 1064 nm and a laser power of 3 $W/cm^2$ for a time period of 4 minutes. Control cells were incubated with the multi-walled carbon nanotubes but were not treated with the NIR laser or were treated with the laser in the absence of nanotubes.

Figure 21:
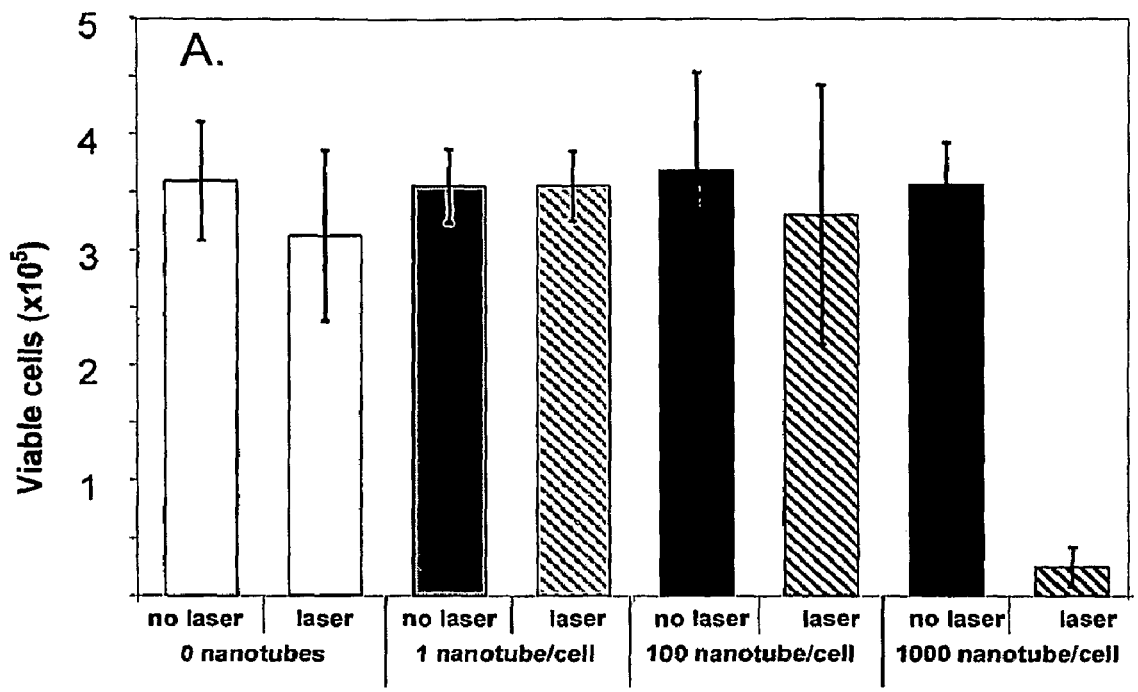
FIG. 21 illustrates cellular viability as a function of carbon nanotube concentration when exposed to near infrared radiation (NIR) according to one embodiment of the present invention.
Figure 22:
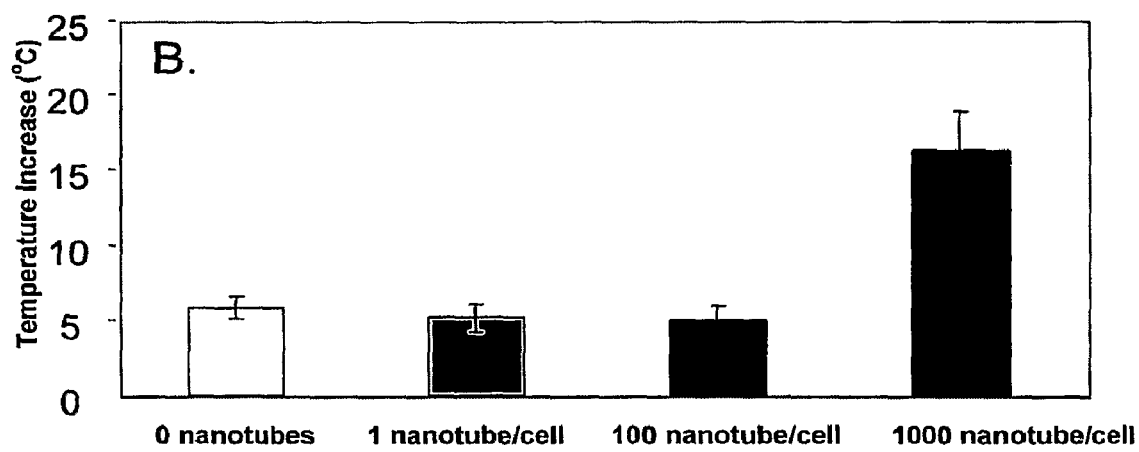
FIG. 22 illustrates temperature increase in a surrounding environment as a function of carbon nanotube concentration according to one embodiment of the present invention.

Viability was assessed in all cultures. As illustrated in FIG. 21, in the absence of the 700 nm multi-walled carbon nanotubes, treatment with NIR laser had no effect on cell viability. As a result, cells display a high transparency to NIR light, and neither exposure to NIR alone nor exposure to nanotubes alone is sufficient to induce cell death. Cells incubated with the 700 nm multi-walled carbon nanotubes and subsequently exposed to NIR demonstrated dramatic dose-dependent decreased in viability, with over 90% cell death at the highest dose tested (e.g. 1000:1). Moreover, the greatest decrease in viability was associated with the greatest increase in temperature. The average number of cells in the 1000:1 nanotube/cell sample decreased by $3.31 \times 10^5 +/- 0.53 \times 10^5$ after exposure to the laser wherein a temperature of 50.7+/−5.7° C. was attained. FIG. 22 illustrates that the greatest temperature increase occurred at a 1000:1 nanotube:cell ratio.

EXAMPLE 10

Regression of Diseased Tissue Treated with Nanotube Compositions

Figure 23:
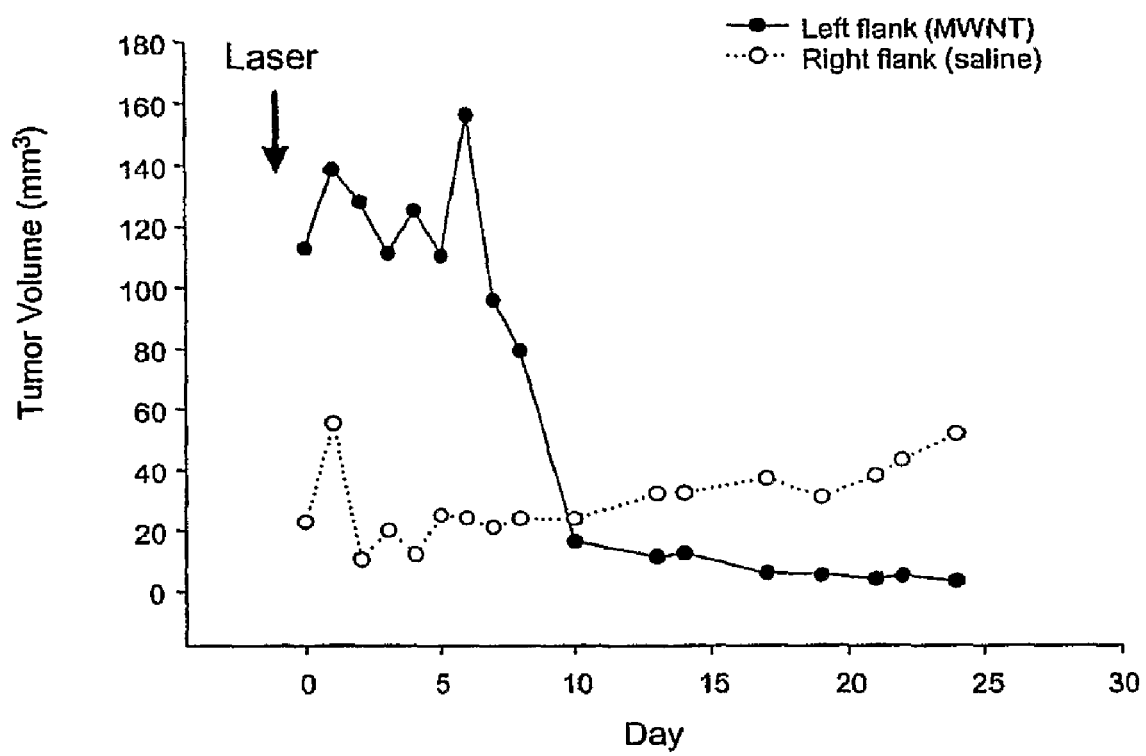
FIG. 23 illustrates the regression of a tumor treated with a multi-walled nanotube composition according to one embodiment of the present invention.

Each flank of a 6-week-old male athymic nude mouse (NCr-nu/nu; NCI, Bethesda, Md.) was inoculated s.c. with $3.0 \times 10^6$ PC3 prostate cancer cells in 0.1 ml serum-free medium (SFM) in a 1:1 ratio with Growth Factor Reduced High Concentration Matrigel (BD Biosciences, San Jose, Calif.). Tumors were allowed to grow until palpable ($\geq$ca 20 $mm^3$). Multi-walled carbon nanotubes (MWNT) containing iron were suspended by sonication in pluronic surfactant PC 127 at a concentration of 0.1% w/w. The multi-walled carbon nanotubes had an average length of about 1200 nm and an average diameter of about 20 nm. The pH was adjusted to 7.3 and NaCl added to 0.9% final concentration. A total volume of 0.1 ml of a 200 μg/ml MWNT suspension was injected directly into the left flank tumor using a sterile 26 g needle. The equivalent amount of saline was injected into the right flank tumor for the control. A single 60 second laser pulse was administered using a YAG laser at a power of 3 $W/cm^2$ to both flank tumors 24 hours after injection of the MWNT. Temperature increase was measured immediately after laser exposure using a thermocouple and was 7.7° C. in the control tumor and 15.8° C. in the treated tumor. Tumor volumes were measured at the indicated times after treatment using calipers. The tumors were of unequal size at day 0 (day 0 is the day of nanotube injection). By day 24, the control tumor had roughly doubled in volume (from 22.7 $mm^3$ to 51.6 $mm^3$) whereas the treated tumor had declined to roughly 2% of its original volume (from 112 $mm^3$ to 2.9 $mm^3$). FIG. 23 illustrates growth of the untreated tumor and the regression of the tumor treated with the multi-walled nanotube composition according to the present example.

EXAMPLE 11

In Vivo Imaging of a Multi-Walled Nanotube Composition Comprising a Contrast Agent Multi-walled carbon nanotubes were produced in accordance with the procedure set forth in Example 1. The multi-walled carbon nanotubes were etched in a mixture of sulfuric and nitric acid ($H_2SO_4$:$HNO_3$=2:1) as follows. 60 ml of sulfuric acid and 30 ml of nitric acid were mixed in a round flask to which 30 mg of multi-walled nanotubes were added. In order to disperse the multi-walled nanotubes in the acid, the mixture was ultrasonicated with a horn sonicator at high power until a black suspension was obtained (usually 20-40 seconds). The flask was subsequently plugged with a glass stopper, and the mixture was sonicated in a sonication bath for 24 hours at constant temperature. The sonication opened the ends of the nanotubes.

After opening, the nanotubes were mixed with a hot oversaturated aqueous solution of $GdCl_3$. 2.5 g $GdCl_3$ was dissolved in 0.9 ml hot deionized water. 5 mg multi-walled nanotubes were added to the $GdCl_3$ solution. In order to homogeneously disperse the nanotubes, the resulting solution was sonicated with a horn sonicator for a few seconds. The solution was subsequently sonicated in an ultrasonic bath for 60 minutes. Every 15 minutes the solution was removed from the bath and heated to dissolve $GdCl_3$ precipitate. After ultrasonication, the $GdCl_3$—multi-walled nanotube solution was stirred at room temperature for five days. After stirring, the solution was diluted with 15 ml of deionized water, and the multi-walled nanotubes were centrifuged down at 1000 g. The supernatant was removed and 15 ml of deionized water were added. The dilution and centrifugation procedure was repeated four times. The final multi-walled nanotube product was filtered through a 0.2 μm filter and dried. ICP elementary analysis and EDX confirmed the presence of Gd in the multi-walled nanotube sample.

A solution of the gadolinium filled multi-walled nanotube was prepared as follows. A 1 wt % aqueous solution of surfactant was prepared. The surfactant used was PLURONIC® F127 available from BASF of Florham Park, N.J. Multi-walled nanotubes comprising gadolinium, as prepared above, were added to the surfactant solution at a concentration of 1 mg/ml. Using a high power horn sonicator, the surfactant—multi-walled nanotube solution was sonicated for 15 minutes.

Figure 24:
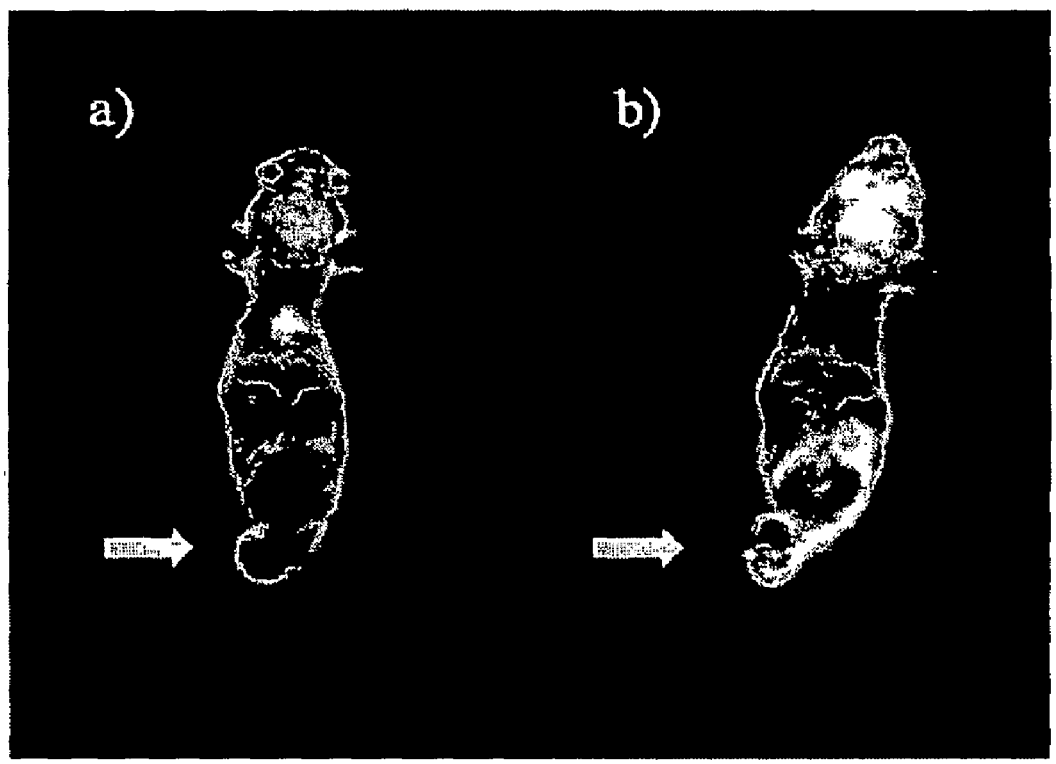
FIG. 24 is a $T_2$ weighted MRI image of a mouse bearing a tumor injected with a composition according to one embodiment of the present invention.

The resulting surfactant-multi-walled nanotube solution was injected into a mouse bearing a tumor on the left back flank. To demonstrate the MRI contrast capabilities of the multi-walled nanotubes comprising gadolinium, the mouse was imaged prior to receiving the injection and subsequent to receiving the multi-walled nanotube injection. FIG. 24 illustrates a $T_2$ weighted image of the mouse (a) before injection of the multi-walled nanotube comprising gadolinium and (b) after injection of the multi-walled nanotube comprising gadolinium. As illustrated in FIG. 24, the multi-walled nanotube composition comprising gadolinium in the nanotubes provided contrast of the tumor.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method for treating disease comprising:
   disposing at least one carbon nanotube, at least one carbon microtube or a mixture thereof in cancerous tissue selected from the group consisting of skin tumors, kidney tumors, prostate tumors, soft tissue neoplasms and bone neoplasms; and
   heating the cancerous tissue with the at least one carbon nanotube, at least one carbon microtube or the mixture thereof, wherein the at least one carbon nanotube or the at least one carbon microtube is doped with boron, nitrogen or a combination thereof.

2. The method of claim 1, wherein the at least one carbon nanotube or the at least one carbon microtube comprises from about 0.01 weight percent to about 30 weight percent nitrogen.

3. The method of claim 1, wherein the at least one carbon nanotube or the at least one carbon microtube comprises from about 5 weight percent to about 10 weight percent nitrogen.

4. The method of claim 1, wherein heating the cancerous tissue comprises irradiating the at least one carbon nanotube, the at least one carbon microtube or the mixture thereof with infrared radiation, microwave radiation or radio wave radiation or combinations thereof.

5. The method of claim 1, wherein the at least one carbon nanotube or the at least one carbon microtube is in the vasculature of a tumor.

6. The method of claim 1, wherein the at least one carbon nanotube or the at least one carbon microtube is not within a tumor cell.

7. The method of claim 1, further comprising killing cells of a tumor wherein killing comprises inducing hyperthermia in the cells of the tumor.

8. The method of claim 7, wherein the volume of the tumor is reduced by at least 50%.

9. The method of claim 1, wherein the at least one carbon nanotube comprises a multiwalled carbon nanotube or the at least one carbon microtube comprises a multiwalled carbon microtube.

10. A disease imaging and treatment system comprising:
    a magnetic field source;
    a radiation source; and
    a thermally inducting contrast agent, wherein the thermally inducting contrast agent comprises at least one carbon nanotube comprising iron, at least one carbon microtube comprising iron or a mixture thereof and the disease comprises cancerous tissue selected from the group consisting of skin tumors, kidney tumors, prostate tumors, soft tissue neoplasms and bone neoplasms.

11. The disease imaging and treatment system of claim 10, wherein the at least one carbon nanotube or the at least one carbon microtube comprises at least 0.1 weight percent iron.

12. The disease imaging and treatment system of claim 10, wherein the at least one carbon nanotube or the at least one carbon microtube comprises from about 0.01 weight percent to about 30 weight percent nitrogen.

13. The disease imaging and treatment system of claim 10, wherein the at least one carbon nanotube comprises a multiwalled carbon nanotube or the at least one carbon microtube comprises a multiwalled carbon microtube.

14. A method of imaging and treating disease comprising:
disposing at least one carbon nanotube comprising iron, at least one carbon microtube comprising iron or a mixture thereof in a cancerous tissue selected from the group consisting of skin tumors, kidney tumors, prostate tumors, soft tissue neoplasms and bone neoplasms;
imaging the cancerous tissue with the at least one carbon nanotube, the at least one carbon microtube or the mixture thereof; and
heating the cancerous tissue with the at least one carbon nanotube, the at least one carbon microtube or the mixture thereof, wherein the at least one carbon nanotube or the at least one carbon microtube comprises from about 0.01 weight percent to about 30 weight percent nitrogen.

15. The method of claim 14, wherein the at least one carbon nanotube, the at least one carbon microtube or the mixture thereof is disposed in the vasculature of a tumor.

16. The method of claim 15, wherein the at least one carbon nanotube or the at least one carbon microtube is not within a tumor cell.

17. The method of claim 15 further comprising killing cells of the tumor wherein killing comprises inducing hyperthermia in the cells of the tumor.

18. The method of claim 17, wherein the volume of the tumor is reduced by at least 50%.

* * * * *